(12) United States Patent
Maples et al.

(10) Patent No.: US 6,913,932 B2
(45) Date of Patent: Jul. 5, 2005

(54) FORMALDEHYDE-AMMONIUM SALT COMPLEXES FOR THE STABILIZATION OF BLOOD CELLS

(75) Inventors: John A. Maples, Miami, FL (US); Lori A. Charie, Pembroke Pines, FL (US); Daniel James Flagler, Miami, FL (US); Rhonda Ann Mills, Pembroke Pines, FL (US); Richard Timmons, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 184 days.

(21) Appl. No.: 10/226,825

(22) Filed: Aug. 23, 2002

(65) Prior Publication Data

US 2004/0038424 A1 Feb. 26, 2004

(51) Int. Cl.$^7$ .......................... G01N 33/00; G01N 1/00
(52) U.S. Cl. ...................... 436/176; 436/8; 436/18; 436/111; 436/128; 436/130; 436/63; 436/69; 422/61; 252/408.1
(58) Field of Search ................ 436/8, 10, 17, 436/18, 106, 111, 128, 130, 164, 166, 172, 174, 176, 808, 518, 519, 63, 69; 422/61, 73; 252/408.1; 435/4, 7.1, 7.2, 7.21, 29, 39, 810, 975, 40.5, 40.51

(56) References Cited

U.S. PATENT DOCUMENTS

| | | | |
|---|---|---|---|
| 5,459,073 A | | 10/1995 | Ryan |
| 5,486,477 A | | 1/1996 | Carver |
| 5,516,695 A | | 5/1996 | Kim et al. |
| 5,529,902 A | * | 6/1996 | Kottke et al. ............... 435/7.21 |
| 5,648,225 A | * | 7/1997 | Kim et al. .................. 435/7.24 |
| 5,820,721 A | * | 10/1998 | Beane et al. ................ 156/276 |
| 6,072,086 A | * | 6/2000 | James et al. ................ 568/449 |
| 6,197,539 B1 | | 3/2001 | Granger et al. |
| 6,197,540 B1 | | 3/2001 | Granger et al. |
| 6,230,713 B1 | * | 5/2001 | Dalesandro et al. ........ 128/898 |
| 6,391,568 B1 | * | 5/2002 | Schneider et al. ......... 435/7.21 |
| 2002/0028517 A1 | | 3/2002 | Brady et al. |
| 2002/0160523 A1 | * | 10/2002 | Wyant et al. ............... 436/501 |

FOREIGN PATENT DOCUMENTS

WO  96/12956  * 5/1996

OTHER PUBLICATIONS

"Platelet Counting by the RBC/Platelet Ratio Method, A Reference Method", *Am. J. Clin. Pathol.*, 2001; 115:460–464.

Puchtler, H., et al, "On the chemistry of formaldehyde fixation and its effects on immunohistochemical reactions", *Histochem.* (1985), 82:201–204.

J.F. Walker, "Formaldehyde", Reinhold Publishing Corporation, New York 1944; pp. 120–123 and 336–341.

Martyak, N.M., et al., "Kinetics of the Reaction of Formaldehyde with Ammonia at 23° C. as Followed by an Ammonia Selective Electrode", *Trans. Inst. Metal Finish.*, 1991 69(2):63–65.

Dahlgran, J.R. et al, "Determination of Formadelhyde and Other Aldehydes in Industrial Surfactants by Liquid Chromatographic Separation of Their Respective 2,4–Dinitrophenylhydrazone Derivatives", *J. Assoc. Off. Anal. Chem.*, 71(3):560–563 (1998).

* cited by examiner

Primary Examiner—Maureen M. Wallenhorst
(74) Attorney, Agent, or Firm—Howson and Howson; Mitchell E. Alter

(57) ABSTRACT

A stabilization reagent composition, particularly desirable for stabilizing blood samples containing platelets, contains reactants that generate multiple species of formaldehyde-ammonium complexes; at least one inhibitor of phosphatase enzymatic activity; and at least one inhibitor of protease enzymatic activity. Blood samples and other tissues are stabilized by this composition. Such stabilized samples are produced by methods for stabilizing the tissue by contacting the sample with the composition.

50 Claims, 12 Drawing Sheets

FORMALDEHYDE-AMMONIUM SALT COMPLEXES FOR THE STABILIZATION OF BLOOD CELLS

BACKGROUND OF THE INVENTION

Cells and biological tissue generally maintain their structure, function, antigen makeup, and chemical constituents within the body. However, once removed from the natural environment of the body, cells and tissue begin to experience immediate changes in these aspects. Thus the preservation and retention of the integrity of cells and biological tissues removed from the body is a continuing challenge in the medical fields, particularly in the fields of blood preservation and organ transplantation.

Circulating whole blood and blood cells are normally quite stable when maintained within the body's environment otherwise disastrous effects would occur due to even small injury. For example, when whole blood is removed from the body, the surrounding environment rapidly changes in parameters such as temperature, pH, and oxygen level. The liquid (plasma) and cellular components in the blood rapidly change in response to changes in temperature and contact with foreign surfaces, such as when drawn into a container. Normally the plasma portion of the blood responds to such change in environmental conditions with the initiation of the coagulation sequence and the subsequent blood clotting. Blood cells, especially those having a physiologic role to most actively respond to environmental changes, lose certain critical physical components and integrity in response to the environmental change. The most sensitive cellular elements in the blood are the short lived blood cells whose function it is to immediately respond to tissue damage and foreign materials such as granulocytes and platelets.

The in vivo state of such cellular components is often represented in the antigen expression of cells as determined by the use of monoclonal antibodies. These antigens are the cluster-designated antigens (CD) present on hematopoietic cells. The appearance or absence of these CD antigens on cells is the basis of cellular identification, characterization and many other clinically useful applications. Changes in the cells are usually initiated by the activation of various cellular enzymes such as phosphatases, protease, oxidases, carboxylase etc. as mediated by (1) a process across the membrane such as receptor binding or surface contact, (2) the exposure to chemicals that are taken up into the cells and cause enzymatic changes such as toxic chemicals, (3) by physical phenomena such as a decrease or increase in temperature. The cellular changes produced in blood cells upon removal from the body are usually represented as the appearance of activated cells, such as are frequently seen with the use of monoclonal antibodies. Thus, the in vivo state of blood is not maintained upon removal from the body.

This tendency of the blood to rapidly change upon withdrawal from the body has proven to be a problem in fields such as cellular analysis and investigational research, and particularly in hematological analysis frequently required for the diagnosis and monitoring of a disease state. For example, it is important to know if the presence of activation associated antigens on blood cells is due to either some aspect of a biological in vivo process or an artifact caused by the in vitro process of obtaining the sample. For accurate research and diagnosis, it is necessary to store and preserve blood and other tissues in a fashion that best represents the in vivo state of that tissue and not the changes caused by removal from the body's environment, such as withdrawal into a container or test tube.

One classical means to prevent changes in whole blood upon removal from the body has been the use of preservatives. The inhibition of the coagulation sequence has been the main objective of conventional anticoagulant preservatives. The classical objective of these anticoagulants for blood analysis was to keep the blood from clotting so that the blood cells could be placed on glass slides for staining and examination. Within the last century these anticoagulants were adapted for use in maintaining certain physical characteristics of the cells such as size and shape. However, while the preservatives maintain cell viability, they nevertheless permit the cells to change in response to the stimulus of the blood drawing process. Thus the use of anticoagulants prevents the plasma from clotting but does not necessarily prevent the changes that occur in the cellular elements. The basis of the most common anticoagulants is the inhibition of coagulation enzymes directly or through the removal of the calcium ions required for many enzymatic processes. Thus blood cells, even in anticoagulated blood, change with time after removal from the body and, when analyzed, may not represent the in vivo state of the blood within the donor. Anticoagulation has most often been accomplished by binding or chelation of calcium ions by a variety of substances such as citrate or ethylenediaminetetraacetic acid (EDTA). Other traditional methods of anticoagulation have involved adding to the withdrawn blood natural enzymatic inhibitors of the coagulation sequence such as heparin or sodium fluoride or hirudin. Such anticoagulants or preservatives, while commonly used for maintaining blood in a liquid state and for the isolation of viable cells for culture, are not designed for maintaining cellular antigens in a representative in vivo state. The longer the cells remain in the anticoagulant the more the cells change due to the effects of the anticoagulant and the effects of storage.

Another approach to blood and tissue preservation has been the use of "fixative" solutions, such as formaldehyde and glutaraldehyde, which react with and cross link the proteins causing them to denature and become insoluble. A variation of this process occurs with the use of dehydrating alcohols, picric acid, mercuric compounds, tannic acid and many other compounds. These historic processes, which are variations of the process for making leather, irreparably alter the structure of proteins. Antigen structures (epitopes) dependent upon defined protein structure are usually destroyed and so is the corresponding ability to react with epitope specific monoclonal antibodies. Even at low concentrations, these fixatives cause cellular changes ranging from the loss of membrane integrity and the lysis of red blood cells to the up-regulation of surface activation antigens.

In a known method of blood and tissue preservation, whole blood is treated with a composition containing a mixture of ammonium-chloride to lyse the red blood cells, enzyme inhibitors and paraformaldehyde. The preserved white blood cells are washed and separated out, thereby producing Beckman Coulter's Immuno-Trol™ cell control product, which maintains the antigenicity of the white blood cells.

With the advent of automated cellular analysis equipment, such as Flow Cytometry, and the invention of monoclonal antibodies, the identification of specific cellular markers on cells and the analysis of cellular attributes and their impact on disease has become a vital component of medical diagnosis and resulting treatment of disease. However, although cellular analysis has changed greatly in the last few years there has been little change in the nature of blood preservation.

For example, U.S. patent application Publication No. US2002/0028517 refers to a method for using the electronic impedance cell counting technique for determining platelet activation by comparing the number of platelets in EDTA preserved samples from which is subtracted the number platelets in a second sample activated with a platelet agonist, such as collagen, ACP, epinephrine and ristocetin solutions, in the absence of EDTA and using the difference as a measure of platelet activity.

Similarly, U.S. Pat. No. 5,486,477 refers to a blood diluent that stabilizes blood cells without fixing the permeability of the cell membranes which includes formaldehyde in a concentration range of 0.01% to 0.15%, an organic buffer, water, and sodium chloride and sodium sulfate, with a base to adjust pH. The disclosure states that no additional reagents are necessary to achieve blood cell stabilization or function as an antimicrobial agent, because numerous additives may interfere with leukocyte membrane permeability.

U.S. Pat. No. 5,459,073 refers to a fixative with low toxicity employing a formaldehyde donor, such as diazolidinyl urea, imidazolidinyl urea, dimethylol-5,5-dimethylhydantoin, dimethylol urea and the like rather than formaldehyde itself.

U.S. Pat. Nos. 6,197,540 and 6,197,539 refer to a stabilized blood composition and method that involves treating separating leucocytes from a blood sample, treating the leucocytes with an aged transition metal solution and reintroducing the treated leucocytes back into the blood sample.

Still other efforts to stabilize blood samples and cellular components of blood have varied. For example, U.S. Pat. No. 5,516,695 refers to a multi-reagent system for analysis of whole blood which contains a non-quaternary ammonium salt, an aliphatic aldehyde having 1–4C, a surface active agent, e.g., saponin, a non-phosphate buffer, e.g., an acetate buffer, and water. This reagent system concurrently lyses RBC and fixes WBC while preserving WBC membranes and surface antigens.

There remains a need in the art for methods and compositions for stabilizing blood and tissue upon removal from the body, to prevent and/or reduces cellular activation and response to environmental change without changing the antigenic makeup of the cells. There remains a need in the art to provide improvement over existing anticoagulants and preservatives in the in vivo representation of the blood drawn from a donor.

SUMMARY OF THE INVENTION

This invention provides a method and composition for stabilizing biological cells and tissues, particular blood samples containing platelets. This method and composition prevents or reduces cellular activation and response to environmental change without changing the antigenic makeup of the cells. In an embodiment of this method, the examples below demonstrate the stabilization and preservation of platelet-associated antigens as a model system for the invention. However, the methods and compositions described herein are also useful to maintain the integrity of other biological cells and tissues.

In one aspect, the invention provides a stabilization reagent composition for use in the stabilization of blood cells, and more particularly, the stabilization of platelet activity. The composition contains reactants that generate multiple species of formaldehyde-ammonium complexes; at least one inhibitor of phosphatase enzymatic activity; and at least one inhibitor of protease enzymatic activity.

In another aspect, the invention provides a stabilized blood sample containing platelets treated with the stabilization reagent composition described herein. The treated sample is characterized by substantially the same state of platelet activation that is found in an untreated blood sample that is measured immediately upon withdrawal from the body. The presence of stabilizer prevents post-withdrawal activation of the platelets in the sample by in vitro environmental conditions. If left untreated, or if treated by other stabilizers in the prior art, the percentage of activated platelets increases over time due to such conditions. This stabilized expression of CD62p on platelets in the reagent-treated sample is maintained for at least 24 hours after said treatment. In one embodiment, the stabilized expression is measured as the presence in the treated sample of ±20% of the number of CD62p positive platelets in the blood sample, when said sample is measured without treatment immediately after withdrawal from the body. In other words, the presence of the stabilizer in the blood samples stabilizes the platelet activation state so that the percentage of CD62p platelets in the stabilized blood sample increases by no more than 20% over the percentage of CD62p platelets in the blood sample measured immediately upon withdrawal. When the treated sample is compared with an untreated sample at some time measured after withdrawal of the samples from the body, the treated sample expresses less CD62p platelets than does the untreated sample.

In a further aspect, the invention provides a method of stabilizing blood cells in a blood sample containing platelets. The method involves contacting the sample with the reagent composition described herein; wherein cells in said sample are characterized as described above. In one embodiment, the sample may also be treated with an anticoagulant or coagulation pathway inhibitor prior to treatment with the stabilization reagent composition.

In yet another aspect, the invention provides a kit containing, inter alia, a first separate component, comprising an aliphatic aldehyde of between 1 to 4 carbon atoms in liquid or powder form or reactants that upon hydrolysis generate formaldehyde; a second separate component comprising a solution comprising an ammonium salt solution, at least one inhibitor of phosphatase enzymatic activity; and at least one inhibitor of protease enzymatic activity; wherein the second component has a physiological pH that does not adversely effect the stabilizing function of the composition; and instructions for mixing the first and second components prior to contacting the mixture with a blood sample containing platelets immediately upon withdrawal from the body.

In still another aspect, the invention provides a method for assessing the efficacy of a blood cell stabilizing reagent. This method includes measuring platelet activation by contacting a blood sample which has been treated with a cell-stabilizing reagent composition described herein with an activating material that activates cellular response by causing physical and/or enzymatic changes in platelets; storing the sample at 20 to 25° C. for 1 to 72 hours; and determining the change in expression of CD62p on platelets in the treated sample compared with the expression of CD62p on platelets in a sample that has not been treated with the reagent composition but has been stored for the same amount of time. The percentage of platelets expressing the CD62p antigen in the samples treated with cell-stabilizing reagent is less than that percentage in an untreated sample stored for the same amount of time.

Other aspects and advantages of the present invention are described further in the following detailed description of the preferred embodiments thereof.

DETAILED DESCRIPTION OF THE INVENTION

Figure 1A:
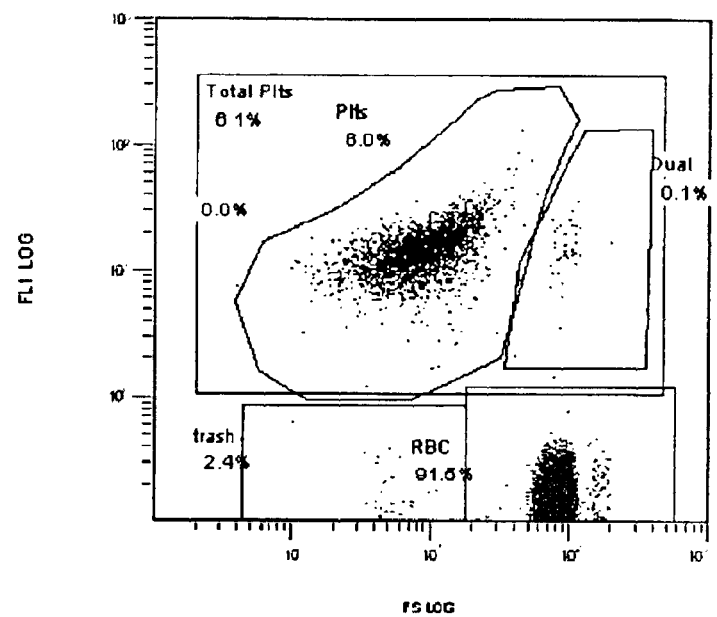
FIG. 1A is a histogram showing normal CD41 (FL1log/ FSlog) expression of fresh EDTA blood preserved with the Stabilization Reagent solution of this invention.

The invention provides a stabilization reagent composition and a kit containing the composition, as well as methods for stabilizing biological tissue using the composition. The term "biological tissue" as used herein, is intended to encompass whole blood, peripheral blood, blood fractions containing cellular components of blood, plasma, and diluted, separated or otherwise manipulated blood samples containing platelets and/or other blood cells (e.g., solutions such as buffered solutions containing cells), cultures containing platelets, solutions or cultures containing other blood cells, and including other non-blood tissues such as urine, saliva, synovial fluid, cerebrospinal fluid, or other fluid secretion. The term "tissue" can include, without limitation, bone marrow and lymph node, as well as samples of other tissues. Alternatively, the sample may be a cell line.

When used to stabilize blood samples or fractions or other tissues containing platelets, the composition and methods of this invention preserve platelet activity in the state of activation substantially the same as that existing at the time of blood or platelet withdrawal from the blood or platelet donor. By "state of activation of the platelets" or "Activation Potential" as used herein is meant the percentage of platelets expressing the CD62p antigen, i.e., the percentage of platelets that bind CD62p fluorescently-labeled antibody as performed by flow cytometry, or CD62p positive platelets in the sample. The CD62p antigen represents a glycoprotein antigen that is unique to megakaryocyte, platelet, and endothelial cell secretory granules. This antigen is only present on the surface of platelets when they are activated. CD62p antigen expression is transient, since the CD62p is rapidly internalized and then degraded in lysosomes.

Generally, in a "healthy" person, a blood sample contains few or no CD62p platelets at the moment of withdrawal from the body. In vitro environmental conditions, e.g., temperature, atmospheric pressure, time, contaminants, etc. effect a withdrawn blood sample so as to activate the platelets by increasing the percentage of CD62p platelets in the sample. Thus, an untreated blood sample or a blood sample stabilized by compositions and methods of the prior art will exhibit over time in vitro an increase in the percentage of CD62p platelets over the "baseline", which is the percentage of CD62p platelets measured immediately in an untreated sample at the time of withdrawal.

In an unhealthy person, a blood sample can contain hyper-activatable platelets or a high percentage of CD62p platelets at the moment of withdrawal from the body. Thus, the baseline for an unhealthy person can be a high percentage of CD62p platelets. The blood samples of such persons over time in vitro tend to exhibit a decrease in the percentage of CD62p platelets, as the antigens fall off of the cells due to in vitro environmental conditions.

The compositions and methods of this invention stabilize in a donor's withdrawn blood sample for at least 24 hours the percentage of CD62p platelets. This percentage in a blood sample treated according to this invention is substantially similar to the percentage of CD62p platelets in the tested donor's baseline. By "substantially similar" is meant that the percentage of CD62p platelets in the blood sample treated according to this invention differs from that of the donor's baseline by no more than about 10 to 30%, and preferably by no more than about 20%. This stabilization of the blood sample thereby enables accurate diagnosis of disease based on percentage of CD62p platelets in blood samples that are stored prior to evaluation. Thus, in the case of a healthy donor, the methods and compositions of this invention permit evaluation of the blood sample by providing a state of platelet activation that is not unduly high due to in vitro environmental conditions. In the case of an unhealthy donor, the methods and compositions of this invention permit evaluation of the blood sample by providing a state of platelet activation that is not unduly low due to in vitro environmental conditions.

Other advantages of the methods and compositions of this invention are discussed below.

I. The Stabilization Reagent Composition of the Invention

A stabilization reagent composition of this invention is characterized by the following essential components, namely, reactants that generate multiple reactive species of formaldehyde-ammonium complexes; at least one inhibitor of phosphatase enzymatic activity; and at least one inhibitor of protease enzymatic activity. Optional components that may be introduced into the reagent include buffers, preservatives, salts, sugars, surface active agents, and enzyme inhibitors other than protease and phosphatase inhibitors.

The reactants that generate multiple species of formaldehyde-ammonium complexes include an aliphatic aldehyde of between 1 to 4 carbon atoms and an ammonium salt solution. Upon interaction, these reactants form multiple complexes or chemically reactive species that contribute to the stabilization of the biological tissue. In one embodiment, one of the species is a hexamethylenetetramine. In another embodiment, one of the species is a methyleneimine. In still another embodiment, one of the chemically reactive complexes is formed by a methylol. In another embodiment, one of the multiple chemically reactive species is a hemihexamine. In another embodiment, one of the reactive species is a cyclotrimethylenetriamine complex containing methylene bridged amino, amido and/or guanidyl groups. Still another complex that is present upon reaction is a complex that cross-links polypeptide chains or proteins on the cell surfaces with methylene bridges. The reactants of the present invention may form some or combinations of these complexes. Still other complexes which are formed by the reaction of aldehydes and ammonium ions can include complexes discussed in K. H. Gustavson, "The Chemistry of Tanning Processes", Academic Press, Inc., New York (1956) at pp. 244–282; J. R. Dahlgran and M. N. Jameson, 1988 *J. Assoc. Off. Anal. Chem.,* 71(3):560–563; N. M. Martyak and B. McDuffie, 1991 *Trans. Inst. Metal Finish,* 69(2):63–65; H. Puchtler and S. N. Meloan, 1985 *Histochem.,* 82:201–204; and J. F. Walker, "Formaldehyde" Reinhold Publg. Corp., New York 1944, incorporated by reference herein. See, also, the NMR data generated and discussed below in Example 1.

Desirably, the aliphatic aldehyde reactant can be formed by bubbling formaldehyde gas into a liquid, e.g., water, or polymerizing formaldehyde to form the powder paraformaldehyde and providing it in solution. Alternatively, it can be a compound that upon hydrolysis generates formaldehyde, such as an ethylene oxide, propylene oxide or butylene oxide. The above-referenced documents provide further teachings concerning the production of formaldehyde and like aldehydes from such compounds, including formalin.

In one embodiment, the aliphatic aldehyde is an aqueous paraformaldehyde or formaldehyde solution, with the aldehyde present at a concentration of between about 0.02 to 1.0% w/v, e.g, by weight volume (grams per 100 ml) in a liquid. In another embodiment, the aldehyde is present at a concentration of up to about 0.8% w/v. The liquid is desirably water or a buffer. Because the chemically reactive species or complexes can be unstable, or stable for only up to about 14 days, it may be desirable to prepare this reactant as a separate component and mix it with the second reactant at approximately the time of use.

Figure 12A:
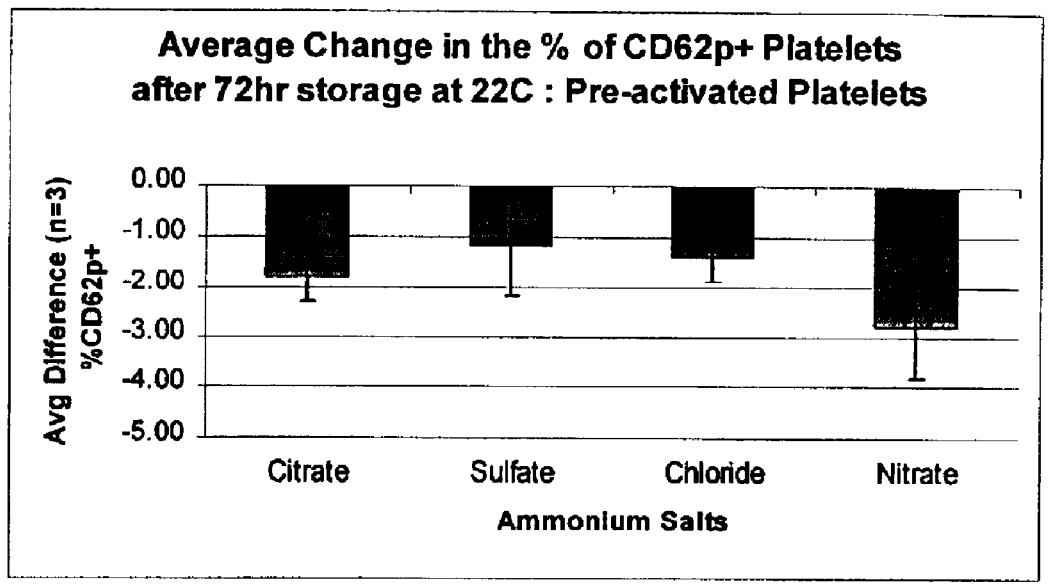
FIG. 12A is a bar graph showing the average change in the percentage of CD62p+platelets (pre-activated) in a blood sample after 72-hour storage at 22° C. The blood sample was treated with stabilization reagents of the invention using different ammonium salts at the same molar concentration. Each solution maintained the performance characteristics described in Tables 5A, 5B and 6.
Figure 12B:
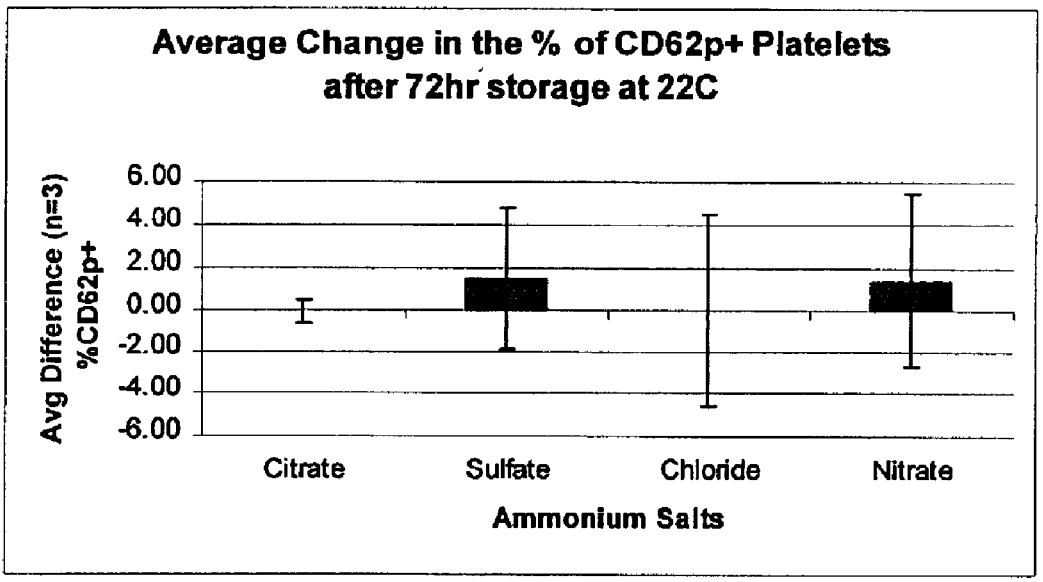
FIG. 12B is a bar graph showing the average change in the percentage of CD62p+platelets (activated) in a blood sample after 72-hour storage at 22° C. The blood sample was treated with stabilization reagents of the invention using different ammonium salts at the same molar concentration. Each solution maintained the performance characteristics described in Tables 5A, 5B and 6.
Figure 13A:
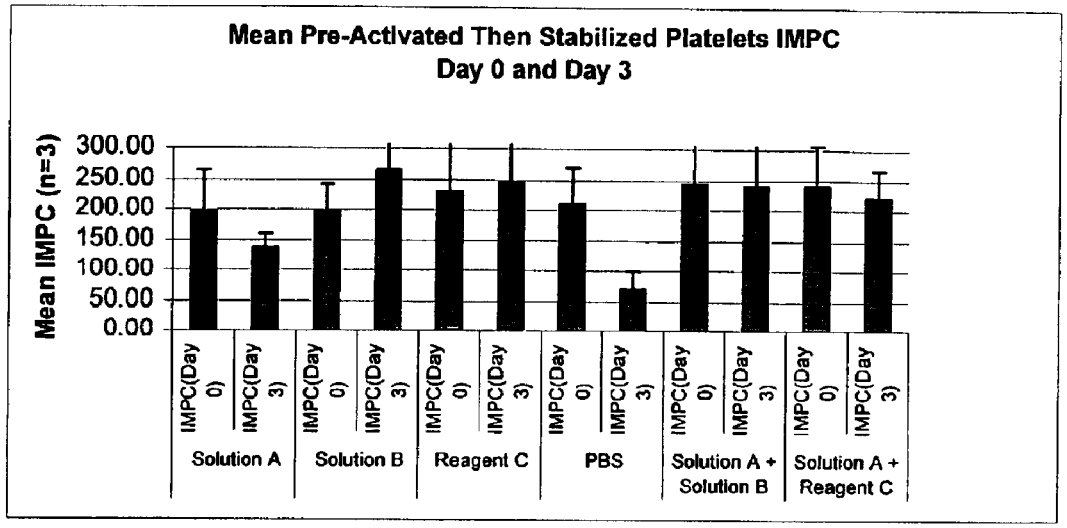
FIG. 13A is a bar graph showing the immune platelet count (IMPC) measured in a blood sample after 72-hour storage at 22° C. on days 0 and day 3 of storage. The blood samples were treated with either Solution A (a combination of ammonium citrate dibasic, and the enzyme inhibitors tetramisole, AEBSF and pyrophosphate) or Solution B (aqueous formaldehyde), Solution C (Tris-buffered formaldehyde), phosphate buffered saline (PBS), a combination of Solutions A and B (which forms a stabilization reagent of this invention), and a combination of Solution A and Solution C (which forms another stabilization reagent of this invention). IMPC is the immuno-platelet count as performed by the method of the International Council for Standardization in Haematology, Expert Panel on Cytometry and International Society of Laboratory Haematology Task Force on Platelet Counting, 2001 "Platelet Counting by the RBC/platelet ratio method: a reference method", *Am. J Clin. Pathol.*, 115:460–464. The combinations of Solution A and Solution B and Solution A and Solution C are superior in maintaining the IMPC and the expression of CD62p during the 72 hours of storage, to any of the solutions when used alone or to the control PBS. The use of organic or inorganic buffers to adjust the pH of the combined or separate reagents does not limit the scope or practice of this invention.
Figure 13B:
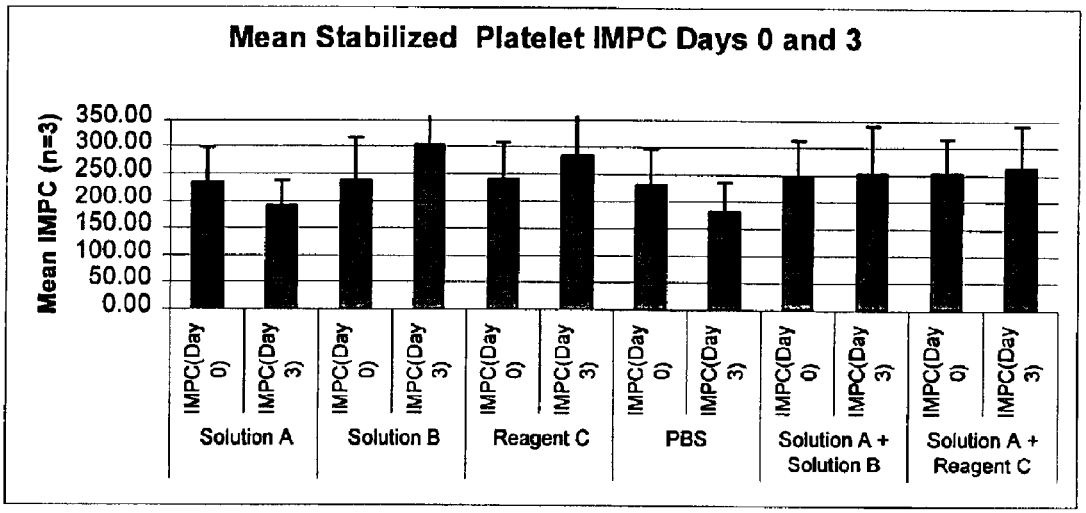
FIG. 13B is a bar graph demonstrating mean stabilized platelet IMPC on days 0 and 3. These platelets were not activated. The goal of maintaining the same platelet count on days 1 and 3 is not met when either the common procedure of just adding a paraformaldehyde solution alone is performed or when simply an ammonium ion solution alone is used. The stabilization reagent of the invention does meet this goal.

The reagent composition of this invention further comprises as a second reactants, an ammonium salt. In the following examples, although ammonium citrate dibasic was chosen for its anticoagulant properties and performance characteristics according to the response surface statistical models, the data indicated that other ammonium salts can be utilized as a reactant to form the desired complexes. Thus, the salt may be selected from the group consisting of dibasic ammonium citrate, ammonium chloride, ammonium fluoride, ammonium nitrate, ammonium sulfate, ammonium persulfate, ammonium sulfamate, ammonium acetate, ammonium carbamate, ammonium carbonate, ammonium phosphate, ammonium lactate, ammonium oxalate, ammonium tartrate, ammonium thiocyanate, ammonium hydroxide, and a combination of any of these ammonium salts. See, for example, the data in FIGS. 12A and 12B in which various ammonium salts were used at the same molar concentration and still maintained the performance characteristics described in Tables 5A, 5B and 6.

Additionally, the selection of the ammonium salt can be manipulated to create a stabilizing reagent to stabilize whole blood, without the lysis of the red blood cells (RBC). For example, the use of ammonium citrate or ammonium sulfate salts in the stabilization reagent, which permit the maintenance of a physiological pH in the range of approximately 6.5 to 7.3 in one embodiment of the stabilization reagent allows use of the stabilization reagent to avoid lysis of RBC. Alternatively, the proper selection and molar concentration of the ammonium salts can produce RBC lysis and still preserve the platelet antigenic expression. The use of ammonium chloride, ammonium fluoride, ammonium oxalate or ammonium nitrate salts in the stabilization reagent allows the use of this embodiment of the reagent to produce RBC lysis, yet preserve the platelet antigenic expression. Thus the selection of the ammonium ion salt reactant for use in the invention is made depending upon the desired performance of the stabilizing reagent, and thus this reagent is useful for the stabilization of biological tissues or materials or solutions containing platelets, in additional to whole blood. The ammonium ion salt is desirably present in the stabilizing reagent composition of this invention at a molar concentration of between about 0.1M to 1.4M. The selection of the desired molarity within that range is within the skill of the art, given the teachings provided herein.

The reagent composition also includes one or more protease inhibitor(s). Desirably, the composition includes multiple such inhibitors. A non-exclusive list of protease inhibitors for use in the present stabilization reagent composition may include the serine protease inhibitors, such as 4-(2-aminoethyl)benzenesulfonyl fluoride hydrochloride (AEBSF), which has a molecular weight of 230.7 and inhibits catalytic activity of the protease active site; antithrombin plasma protein (60,000 MW) that inhibits thrombin and other serine proteases in the blood clotting cascade; or 4-amidinophenylmethanesulfonyl-fluoride-HCl (APMSF, 352.7 MW), an irreversible inhibitor of trypsin-like serine proteases. Still other serine proteases include Aprotinin (6500 MW) that inhibits serine proteases by tightly binding to the active site of the enzyme; diisopropyl phosphorofluoridate (DFP, 184.2 MW), a very toxic, irreversible inhibitors of serine proteases and acetylcholine esterase; phenylmethanesulfonyl fluoride (PMSF, 174.2 MW), which is another toxic, irreversible inhibitor that acts by chemically modifying the active site of the enzyme; and α-toluenesulfonyl fluoride.

Other suitable serine and cysteine protease inhibitors useful in the stabilization reagent include antipain (678.2 MW), a reversible inhibitor of proteasese and of RNA synthesis; chymostatin (600 MW), a reversible inhibitor of some serine and cysteine proteases; leupeptin (475.6 MW) a reversible competitive inhibitor of trypsin-like proteases; L-1-chloro-3-[4-tosyl-amido]-7-amino-2-heptanone-HCl (TLCK, 369.3 MW), which inhibits irreversibly by chemically altering the enzyme active site; and L-1-chloro-3-[4-tosylamido]-4-phenyl-2-butanone (TPCK, 351.8), which irreversibly inhibits by chemically altering the enzyme active site.

Other suitable cysteine protease inhibitors useful in this invention include E-64 (357.4 MW), a non-competitive irreversible inhibitor of cystein proteases. Other suitable protease inhibitors inhibit metaloproteases. For example, amastatin (511 MW) is a non-toxic reversible inhibitor; bestsatin (244.8 MW) is a multi-function metallo-protease inhibitor that has anticarcinogenic and immunomodulating properties; diprotin (341.5 MW), a reversible inhibitor; EDTA (372.3 MW) a reversible inhibitor that acts by chelating enzyme cofactors and may interfere with other metal dependent biological processes. Other metaloprotease inhibitors include vanadium, molybdate salts, and 1,10-phenanthroline. Still other suitable inhibitors for use in this invention are aspartic protease inhibitors, such as pepstatin (685.9 MW) a peptide that provides reversible inhibition.

In one embodiment, the stabilizing reagent of this invention includes a single protease inhibitor. In another embodiment, the stabilizing reagent of this invention includes combinations of two or more such inhibitors, to permit use of small amounts of those inhibitors that are toxic or cause otherwise undesirable effects if used alone in large concentrations. It is desirable for the concentration of protease inhibitor(s) in the stabilizing reagent composition to be up to about 10 mM. However, the range of concentrations is entirely dependent upon the inhibitor(s) used. This range is determined based upon the experimental data of inhibition of platelet activation, as described herein. One of skill in the art given the teachings provided herein would readily be able to determine, with only a minimal and conventional amount of experimentation, a desirable concentration for each specific inhibitor used in the stabilization reagent.

Yet another component of the stabilizing reagent composition is one or more phosphatase inhibitor(s). A non-exclusive list of suitable phosphatase inhibitors includes, without limitation, pyrophosphate, microcystin LA, microcystin LR, tetramisole, L-4-bromotetramisole, tautomycin, okadaic acid, calyculin, thrysiferyl-23-acetate, cantharidine, vanadium salts, sodium orthovanadate, tartrate salts, phloridzin, molybdate salts, and imidazole. For other suitable inhibitors, see Handbook of Enzyme Inhibitors, Melmward Sollner (1989), ISBN 3-527-26994-0; ISBN 0-89537-860-0, incorporated by reference herein.

In one embodiment, the stabilizing reagent of this invention includes a single phosphatase inhibitor. In another embodiment, the stabilizing reagent of this invention includes combinations of two or more such inhibitors, to permit use of small amounts of those inhibitors that are toxic or cause otherwise undesirable effects if used alone in large concentrations. It is desirable for the concentration of a phosphatase inhibitor(s) in the stabilizing reagent composition to be up to about 120 mM. However, the range of concentrations is entirely dependent upon the inhibitor(s) used. This range is determined based upon the experimental data of inhibition of platelet activation, as described herein. One of skill in the art given the teachings provided herein would readily be able to determine, with only a minimal and conventional amount of experimentation, a desirable concentration for each specific inhibitor used in the stabilization reagent. In the examples below, three such inhibitors are used in the stabilizing solution, i.e., tetramisole in a concentration of 10–60 mM, AEBSF in a concentration of up to 10 mM and pyrophosphate decahydrate ($10*H_2O$) in a concentration of up to 50 mM.

The reagent of this invention can be adjusted in formulation to optimize its performance per specific application. For example, depending upon the selection of the components, the stabilizing reagent composition of this invention has a pH in the physiological range of between 4.5 to 8.0. The reagent composition is also characterized by a range of useful osmolarity. The addition of components or the dilution with water can be easily accomplished to produce osmolarity ranges within the standard physiologic ranges of blood and urine, i.e., 250 to 1200 mOsmo. Generally, the reagent will be iso-osmotic. Preferably, the osmolality is from about 318 to about 340 milliOsmo/kg (mOsm/kg). More preferably, the osmolality will be from about 321 to about 337 mOsm/kg. Most preferably, the osmolality will be from about 325 to about 335 mOsm/kg. However, the osmolarity of the reagent can vary depending upon whether the reagent is intended to lyse or not to lyse RBC. The volume of the reagent can however be adjusted to effect an optimum final osmolarity when admixed with a blood sample. The appropriate pH and osmolarity may be achieved by the required reactants and proteases forming the composition, as described above. Alternatively, the reagent composition may also include an inorganic basic salt or an organic basic compound for adjusting the pH range of the composition to within the appropriate range. Thus, the reagent may additionally comprise a buffer that provides a physiological pH and does not adversely affect the stabilizing function of the composition.

Suitable buffers include those that maintain the pH of the composition in the range of about 4.5 to about 9, depending upon whether it is desired for the stabilization reagent to lyse RBC, as discussed above. More preferably, a pH in the range of about 4.5 to 8 is obtained. The buffer may be selected from a variety of buffers known to those of skill in the art to be used in the compositions of the invention and include, without limitation, phosphate buffered saline (PBS) or isotonic saline, such as ISOTON®II diluent, U.S. Pat. No. 3,962,125, [Beckman Coulter, Inc., Miami, Fla.], Tris buffer, the organic buffer N-(2-Acetamido)-2-iminodiacetic acid (ADA), or Pyrophosphate buffer or combinations thereof. Also useful are acetate buffers, succinate buffers, maleate buffers, citrate buffers, imidazole buffers, carbonate buffers, MES buffer, MOPS buffer, and HEPES buffer, among many that may be readily selected by one of skill in the art. Still other buffers such as the Good buffers identified in Good, N. E. et al. 1966 *Biochemistry* 5, 467 and Good, N. E., and Izawa, S. 1972 *Methods Enzymol.* 24, 53 may be utilized depending upon the functional requirements of the formulation as determined by one skilled in the art.

Additionally, such buffers may also be used to adjust the concentration of one or more of the components of the composition of this invention. In the stabilizing reagent composition of this invention, the optional buffer may be present in up to 50% by volume. Of course, if the buffering provided by the ammonium salt solution is sufficient, the optional buffer is not used in the stabilization reagent.

Still other optional components of the stabilizing reagent of this invention may include preservatives, anticoagulants, detergents, dyes, and stains. A non-exclusive list of useful preservatives includes, but is not limited to, 5-Chloro-2-methyl-4-isothiazolin-3-one, and 2-methyl-4-isothiazolin-3-one under the trademarks ProClin 300 or ProClin 150, methyl, propyl, ethyl butyl parabens, imidazolidinyl urea, diazolidinyl urea, iodopropynyl butylcarbamate (e.g., under the trademark GERMALL®), alone or in combination with others.

In one embodiment of this invention, the aldehyde reactant is prepared as a separate solution for admixture with the ammonium ion salt solution. Generally, the inhibitors may be in the ammonium ion salt reactant solution. Other components may be mixed and stored separately. This enables the end user to mix the aldehyde reactant with the ammonium ion reactant in proximity to use with the biological tissue, thereby preserving the integrity of the most useful chemically reactive complexes described above. One such two-part embodiment of the stabilizing reagent composition of this invention contains as the ammonium ion salt solution Reagent A, which contains 57.06 mg/ml ammonium citrate, dibasic with the alkaline phosphatase inhibitors (9.63 mg/mL tetramisole.HCl and 44.64 mg/mL sodium pyrophosphate, decahydrate), and the serine protease inhibitor (0.096 mg/mL AEBSF). Reagent B contains 10 mg/mL paraformaldehyde, 0.4 mL/mL sodium hydroxide, 1N, and an optional buffer (60.5 mg/mL Tris). These Reagents are mixed in a 1:1 ratio by volume to provide an exemplary stabilizing reagent composition of this invention.

The stabilizing reagent composition of this invention may be further characterized by the manner in which it affects cells, as described above For example, the use of this stabilizing reagent stabilizes expression of the cell surface antigen, CD62p, on platelets in a blood sample or other sample containing platelets to a state substantially similar to that of the baseline, i.e., the untreated blood sample when this sample was measured immediately after withdrawal from the donor. The stabilized sample after 24 hours contains ±20% of the number of CD62p positive platelets that were present in the untreated blood sample when this sample was measured immediately after withdrawal from the donor.

This measurement may be accomplished as described in detail below. In fact, this functional characteristic of the stabilizing reagent is true when the blood sample is withdrawn and immediately measured, or withdrawn from the donor, treated with an anti-coagulant or a coagulation pathway inhibitor, and measured for the presence of the antigen. More particularly, when fresh whole blood from a healthy donor is drawn into the stabilizing reagent composition, the platelets are not activated. Treatment with the stabilizing reagent enables the platelets to maintain their state of activation from the time that they are treated, e.g., at the time the platelets are withdrawn from the donor's body or, at the time the platelets are being drawn into a tube, etc. This ability to preserve platelet activity with the reagent composition is a characteristic of this composition that stands in stark distinction to the prior art compositions and methods that may activate all of the platelets in withdrawn blood samples.

In one embodiment, the stabilization reagent and methods described below can preserve human cells present in whole blood samples by "freezing" the cells in the blood sample in the state by which the cells were characterized when the reagent is introduced to sample. This stabilization of the cells is functional, not mechanical. Thus, following stabilization, the stabilized cells cannot be induced to a new functional state. The reagent minimizes change in cells over time and generally preserves more antigens than other known stabilization methods. See comparative Examples 6 and 7 below. However, the reagent may not preserve all antigens, nor can the reagent recover antigens lost/shed before its introduction into the sample.

The reagent also minimizes the loss of granules and other intracellular change in the biological sample, potentially allowing more cellular components to be available for analysis. The presence of cellular elements is, for the most part, dependent on the age of sample and whether the donor of the sample is abnormal in some manner that affects sample stability. Further, with regard to light scatter characteristics, the reagent is useful in preserving flow cytometry-like scatter (FALS and SS). Use of the reagent compositions of this invention in the stabilization of cells and tissues provides consistency and reproducibility in cell analysis over time.

In contrast to the standard formaldehyde-only fixation method for the retention of antigen expression in withdrawn cells of the prior art, the cells preserved with the reagent composition and methods of this invention are available for a broader range of analyses. As demonstrated by the following examples, the reagent of the present invention stabilizes internal antigens within the cell and stabilizes external (cell surface) antigens on the cell. The reagent further preserves the light scatter characteristics of the cells and reduced endogenous phosphatase in tissue samples. Thus, this reagent is useful as a general cell preservative, as a reagent in DNA and RNA studies, in platelet enumeration methods, in the assessment of platelet reactivity, e.g., for platelet/leukocyte aggregate studies, in the study of anticellular (auto) antibodies and plasma (soluble) analytes, among other uses.

II. Stabilized Tissues

Another embodiment of this invention is thus a stabilized sample of biological tissue, as defined above, preferably blood or a solution containing platelets, treated with the stabilizing composition as described above. The sample is characterized by a decreased state of activation, particularly platelet activation. The sample is also characterized by a stabilized expression of CD62p antigen on platelets in the sample for at least 24 hours after treatment with the stabilizing reagent. Stabilized expression measured as the presence in the treated sample is ±20% of the number of CD62p positive platelets in the baseline, i.e., an untreated sample measured immediately after withdrawal from the body.

III. Methods of Stabilizing Tissue and Assessing Efficacy of Stabilization

In another embodiment, the invention provides a method of stabilizing blood cells in a biological sample containing platelets. In one embodiment, such a sample is a whole blood sample. In other embodiments, as stated above, the sample may contain platelets, e.g., a blood fraction or solution. As described below in more detail and in the examples, whole blood is contacted with the stabilization reagent and incubated for approximately one hour. After this incubation period the platelets, as measured by CD62p expression, no longer respond to a phorbol ester activation agent and continue to maintain the same level of CD62p expression for seven days or longer.

More specifically, the method involves contacting the sample with the reagent composition as described above. Preferably, the sample and reagent composition are in a 1:1 ratio. Since an important feature of the stabilization reagent is the number of molecules of the complexes in the stabilization reagent per cell, the stabilization reagent may be diluted, e.g., in saline, and still function. As one example, a large dilution with saline may be made and only a small amount of blood added to achieve the same number of total molecules per cell, but at a much lower absolute concentration of the stabilization reagent reactants. If the stabilization reagent had a low concentration, a large amount could be used, resulting in a ratio of 1:100 or greater. The ratio is generally adapted to what is customary and practical for laboratory use. In one embodiment, in which the aldehyde solution is mixed with the ammonium salt solution as described above, immediately prior to the contacting step, it is desirable that the desired volume of sample, e.g., blood, is added to the pre-mixed stabilizing composition, rather than adding the composition to the blood sample. Desirably, the blood/reagent composition is mixed gently, such as by inverting a suitable container containing both the sample and the composition about 3 times. It is further preferred that the mixed sample remain in contact with the composition for at least about 1 hour at room temperature, e.g., approximately 24–28° C. However, in general, the time for sufficient inhibition to occur can vary with the sample, and the minimum or maximum times necessary for inhibition to occur for any particular sample can be determined by routine experimentation, if one hour is not sufficient.

This method stabilizes the biological sample, e.g., blood sample, in the activation state that characterized the sample at the moment of withdrawal from the donor and contact with the reagent composition. As expected, the sample should be contacted with the stabilizing reagent as soon as it is withdrawn, because alterations in the activation state of biological tissue, especially blood, begins almost immediately upon withdrawal from the donor.

The reagent composition and methods can be used independently of, or in concert with, traditional anticoagulants and provide cellular stabilization that prevents the changes in activation antigens that would occur with the use of the anticoagulant alone. As an alternative or additional step of this method, the biological sample, e.g., blood sample, may first be drawn into a conventional calcium chelating anticoagulant or a coagulation pathway inhibitor prior to contacting the sample with the stabilizing reagent. Conventional anticoagulants or coagulation pathway inhibitors include, without limitation, ethylenediaminetetraacetic acid (EDTA) or a salt thereof a citrate salt, sodium fluoride, hirudin and heparin, or combinations thereof, as used in common commercially available blood collecting tubes/containers.

The sample, once treated with this method, contains cells characterized by a state of activation substantially similar to that of the baseline and a stabilized expression of CD62p on platelets for at least 24 hours after treatment. The stabilized expression can be measured as the presence in the treated sample of ±20% of the number of CD62p positive platelets that were present in the sample, when said sample is measured without treatment immediately after withdrawal from the donor's body.

In another embodiment, this method may be further modified by adding steps for determining the activation status of the platelets. Alternatively a separate method for determining activation status may be performed to assess the efficacy of any stabilization reagent. A method for assessing the efficacy of a blood cell stabilizing reagent or measuring the stabilization effect of a stabilization reagent according to this invention comprises the steps of:

(a) measuring platelet activation by contacting a blood sample which has been treated with a cell-stabilizing reagent composition, and a sample not treated with the stabilizer, with an activating material that activates cellular response by causing physical and/or enzymatic changes in platelets. The activator provides the maximum state of platelet activation possible;

(b) storing the samples at 20 to 25° C. for 72 hours; and (c) determining the change in expression of CD62p on platelets in the treated sample compared with the expression of CD62p on platelets in a sample that has not been treated with the stabilizer reagent composition but has been stored for the same amount of time. According to this method, the percentage of platelets expressing the CD62p antigen in the stabilizer treated samples is less than that percentage in an untreated sample. Once the blood is treated with the stabilizer, the platelets do not respond to the activating material and the state of activation is substantially similar to that of the baseline. Blood not treated with the stabilizer will respond to the activating material by expressing more CD62p up to the maximum possible. Therefore, stabilizer treated blood plus activating material will have less CD62p-expressing platelets than blood not treated with stabilizer. In this case the addition of an activating agent would be expected to increase the number of CD62p positive platelets in the untreated samples and not the "reagent treated" samples. Thus the stabilizing reagent "prevents" exogenous activation.

Such platelet activation may be measured by adding to a sample of biological tissue shortly after withdrawal from a donor (either stabilized or unstabilized samples, depending on the measurement being sought) an activating material that activates cellular response by causing physical and/or enzymatic changes in platelets. Preferably for use in this method, the activating material is a solution of phorbol 12-myristate 13-acetate (PMA). The PMA is added to a final concentration of between about 0.001–5 $\mu$M in the sample. Standard activation agents known to be useful for platelet studies, such as collagen, thrombin, ADP, calcium ionophores, and the like are useful in addition to or in place of the PMA. See, e.g., K. S. Authi et al, 1994 "Mechanisms of Platelet Activation and Control", *Adv. Exp. Med. Biol.*, 344, Plenum Pub Corp; ISBN 0306446316; and Alan Michelson, 2002 "Platelets", ISBN 0124939511.

Once treated with the activating material, the sample can be stored at about 20 to 25° C. for up to about 72 hours. Storage time is optional. It is expected that normal time periods required for specimen transport from the donor to the label or normal mail shipping times for biological materials will fall within the optional storage times.

Expression of CD62p is measured typically by flow cytometric analysis using dual or multi-parameter analyses, and particularly by staining the samples with labeled ligands that bind to CD62p on the platelets in the sample. The ligands are conventionally monoclonal antibodies to the antigen to be measured. Typically, anti-CD62p antibody and anti-CD41p antibody, suitably labeled are used. Alternatively, antibodies to any cell surface antigen known to be present on hematological cells are useful, including without limitation, antibodies to CD61, CD42a, CD42b, CD9, CD36 and the like. See, e.g., A. N. Barclay et al, The Leukocyte Antigen Facts Book, 2nd edit., Academic Press, San Diego, Calif., publ. (1997), for lists of other cell surface antigens, for which antibodies can be used according to this invention. These antibodies are typically labeled with fluorescent labels, such as phycocyanin, allophycocyanin, allophycocyanin B, phycoerythrin, R-phycoerythrin, fluorescein isothiocyanate, phycoerythrocyanin, phycoerythrin-texas red, PE-Cy7, allophycocyanin-Cy5, and allophycocyanin-Cy7, among others.

According to this method, the change in expression of the CD62p antigen on platelets in the stabilized sample from a donor is compared with the expression of CD62p on platelets in an untreated sample from a normal donor, both samples stored for the same amount of time. Four parameters are obtained from the stabilized and unstabilized samples. Parameter A represents the in vitro activation of sample that would normally occur without stabilization or is defined as the percentage of CD62p positive platelets in an anticoagulated blood sample from a normal donor containing no stabilization reagent composition. Parameter B is defined as representing the inhibition of in vitro activation of the stabilized sample or the percentage of CD62p positive platelets in the same anticoagulated blood sample from a normal donor incubated with the stabilization reagent composition, preferably for about one hour. Parameter C is defined as the maximum CD62p expression due to activation in the same normal, non-stabilized sample or the percentage of CD62p positive platelets in an anticoagulated blood sample containing no stabilization reagent composition to which PMA is added to a concentration between 0.001 $\mu$M and 5 $\mu$M and incubated for up to one hour. Parameter D represents the inhibition of the activation agent in the stabilized sample and is the percentage of CD62p positive platelets in the anticoagulated blood sample containing the stabilization reagent to which PMA is added to a concentration between 0.001 $\mu$M and 5 $\mu$M and incubated for up to one hour.

That the stabilization reagent of this invention functions to stabilize the activation status of a percentage of CD62p positive platelets in the treated sample is evidenced by the formula

[Parameter C (the maximum activation of sample) minus Parameter A (the in vitro activation of the sample)] is greater than [Parameter D (the maximum activation of the stabilized sample) minus Parameter B (the in vitro activation of the stabilized sample).

This formula demonstrates that the difference in the percentage of CD62p positive platelets in untreated samples (i.e., Parameter C minus Parameter A) is greater than the difference in stabilized samples (i.e., Parameter D minus Parameter B). More particularly, the method using the stabilization reagent of this invention demonstrates that the difference in the percentage of CD62p positive platelets in the stabilized sample (i.e., D minus B) is maintained +/−20% of the baseline or the immediately stabilized sample for at least 24 hours. The CD62p values do not change more than 20% from the baseline in the stabilized samples. In a normal sample, this CD62p would likely be a low value and not increase. Alternatively, in an abnormal sample, the CD62p value is likely to be a higher value that does not increase or decrease.

Another measurement that proves the efficacy of the stabilization reagent and method is represented by the stabilized samples maintaining for a period of at least 24 hours the difference between (Parameter D) minus (Parameter B) to within 80% of the original value determined within the first hour after addition of PMA.

Thus, the stabilization reagent provides a better representation of the in vitro state of the sample, even in the worse case scenario, where the blood is being activated, i.e., the clinically important situation. As one embodiment of the use of this invention, the examples below describe how the compositions and methods of this invention improve the ability to determine in vivo blood platelet activation state by maintaining CD62p antigen expression post blood drawing. This stabilization improves the diagnostic capability of blood cell analysis. For example, the composition and methods are used to stabilize the activation state of platelets as demonstrated with the use of the monoclonal antibody to platelet CD62p antigen.

It should be clear to one of skill in the art that this method may be altered by the selection of the platelet cell surface antigen to be measured, the activating material, the antibody and label (e.g., platelet monoclonal antibody-dye conjugate) selected, as well as the incubation and/or treatment parameters of the method. One of skill in the art may readily modify this method by resorting to known materials and techniques available in the art without departing from the invention.

IV. Kits of the Invention

In yet another aspect of this invention, a kit is provided for performance of the above-described methods or obtaining the compositions of this invention. Preferably such kits are employed for performing the diagnostic methods of this invention. However, such kits can be assembled for research purposes in developing and evaluating other stabilizing reagents.

The stabilizing reagents, the components thereof, as well as components necessary to perform any number of variations of the methods described above may desirable by assembled into a kit for convenient use. Such a kit may contain the reactants useful to form the stabilizing reagent or to use in the method as two separate components. For example, one separate component present in a separate container is an aliphatic aldehyde of between 1 to 4 carbon atoms in liquid or powder form or reactants that upon hydrolysis generate formaldehyde. In a preferred embodiment, the first component of the kit is a 0.5 to 1% aqueous formaldehyde solution. A second separate component present in a second container is a solution comprising the ammonium salt. The inhibitor(s) of phosphatase enzymatic activity may be provided as a separate component or may be provided as part of the component containing the ammonium salt solution. The inhibitor(s) of protease enzymatic, activity may be provided as a separate component or may be provided as part of the component containing the ammonium salt solution. Thus, in one embodiment of the kit, the second separate component contains the ammonium salt solution and one or both types of inhibitors. In still another alternative kit, the phosphatase inhibitor(s) and the protease inhibitor(s) may be provided in combination in a single component, distinct from the formaldehyde solution component and the ammonium salt solution component described above. Any of the optional components identified above may also be included in the second component, or in additional containers as additional components. The second (and additional, if any) component(s) has a physiological pH that does not adversely effect the stabilizing function of said composition formed when the reactant components are mixed. In one embodiment, the second component contains an ammonium dibasic salt and multiple protease and phosphatase inhibitors, and an optional buffer.

Alternatively, the stabilizing reagent may be provided in the kit pre-mixed in a single container.

Such a kit further contains instructions for mixing the separate components, if present, prior to adding a volume of a sample containing platelets (e.g., blood) immediately upon withdrawal from the donor's body to the stabilizing reagent. The kit may further contain platelet monoclonal antibody-dye conjugates, for measuring CD62p positive platelets, such as CD62p-PE and CD41-PC7, among others. The kit further comprises instructions and reagents for performing measurement of CD62p antigen expression on platelets.

The kit further comprising at least one of the following additional components selected from the group consisting of suitable vessels for containing samples, suitable controls or tables of normal or disease-characteristic values of activated platelets; an anti-coagulant or coagulation pathway inhibitor, other reagents suitable for the performance of flow cytometric analyses and combinations thereof; suitable diluents and buffers for the samples, disposable gloves, decontamination instructions, applicator sticks or containers, and sample preparator cups.

The kit of the present invention can contain either the same or different detectable labels, whereby a plurality of samples can be examined. These kits can additionally contain reagents necessary to maintain or preserve the samples. More importantly, the kit contains instructions for performing the methods of stabilizing the sample and methods of assessing the stabilization effect and preparing the controls. The kits preferably also contain necessary buffer substances or media, as required. One of skill in the art could assemble any number of kits with the information and components necessary to perform the method on a biological sample for any specific cell surface antigen and target cell, and compare the results to norms for that cell population to detect signs of disease or abnormality in platelet activation status.

V. EXAMPLES

The following examples demonstrate the composition and methods of the present invention in the stabilization of whole blood. The following examples illustrate various aspects of this invention. These examples do not limit the scope of this invention, which is defined by the appended claims.

Example 1

Analysis of the Complexes Formed by the Reactants Present in the Stabilization Reagent In one experiment performed to generate the stabilization reagent composition of this invention, the reagent was generated by using ammonium citrate and formaldehyde as the reactants. Complexes formed thereby were demonstrated by the shift in the NMR data indicated in Table 1 below. In Table 1, the hydrogen atom in bolded type illustrates the proton measured. T=0 means that the shift was observed immediately post-mix for the stabilized reagent composition of the invention and at one time for the components of the reagent individually. T=14 indicates storage for 14 days post-mix of the components of the reagent composition of the invention.

TABLE 1

NMR Data

| Composition | Proton Type | Theoretical Shift | Observed Shift T = 0[A] | T = 14 post-mix |
|---|---|---|---|---|
| Formaldehyde Alone ($CH_2O$) | RCHO | 9–10 | 8.32 | — |
|  | ROH | 1–5.5 | 4.69 | — |
|  | HC—OH | 3.4–4 | 3.22 | — |
| Ammonium Citrate Alone ($C_6H_{14}N_2O_7$) | HC—$CO_2$H | 2–2.6 | 2.51–2.65 | — |
| Stabilization Reagent of the Invention | HC—$CO_2$H | 2–2.6 | 2.51–2.65 (4 peaks) | No change |
|  | HC—OH |  | 3.20 |  |
|  | HC—OH | 3.4–4 | 3.24 |  |
|  | $R_2$CH—X |  | 4.5–4.65 (cluster) | Changes in peak heights |
|  | ROH | 1.5–5 | 4.67 |  |
|  | $RNH_2$ | 1–5 | 4.75 | New peaks present |
|  | RCHO | 9–10 | 8.29 |  |

The summary of these results is as follows. Formaldehyde was measured alone and the observed shifts demonstrated agreement with the published theoretical shift values in the expected Proton Type of the listed components (theor. shift). Ammonium citrate was measured alone and also demonstrated expected agreement with the published Proton Type shift for ammonium citrate.

When the ammonium citrate and formaldehyde solutions are combined to form a reagent composition of this invention with the essential inhibitors, several new peaks were seen that represent new Proton Type shifts that were not representative of the components/protons formed by NMR analysis of either of the ammonium citrate alone or formaldehyde alone. Therefore, a chemical reaction occurs immediately upon mixing formaldehyde and ammonium citrate solutions, as evidenced by the appearance of new peaks in the NMR spectra.

Some of the new peaks in the NMR spectra correspond to molecular species consistent with those postulated to form in the reaction of formaldehyde with ammonium salts, specifically methyleneimine. See J. F. Walker, "Formaldehyde", Reinhold Publishing Corp, American Chemical Society Monograph Series (1944), from E.I. du Pont de Nemours & Company, Inc., pages 120–341. The predominant production of methyleneimines and hexamethylenetetramines that Walker proposed was not apparent in the t=0 NMR peaks of Table 1. After storage for 14 days, some new peaks were present that could correspond with the methylenimine postulated. Alternatively, the reaction of formaldehyde and ammonium salts yields methylols, which proceed to form methylene bridges with amides, which may be responsible for the stabilization of the reagent composition of this invention. The additional peaks in the NMR spectra are also consistent with methylols.

While the most dramatic changes in the NMR spectra appear to occur immediately upon mixing, subtle changes were observed over a two-week period. Although the major reactive and functional components are rapidly formed and maintained, these NMR changes indicate that the reaction is not at an endpoint. The use of a two part reagent is desirable for maintaining consistent reagent performance. It is speculated that the functional component may be associated with reactive methylols formed as described by H. Puchtler and S. N. Meloan, 1985 *Histochem.*, 82:201–204. Without wishing to be bound by theory, the resulting complexes were the effective component in the preservation of cellular antigens and light scatter characteristics as indicated in the Examples below.

Without wishing to be bound by theory, the inventors postulate that it is likely that the reaction of formaldehyde and ammonium salts in the presence of the requisite proteases yield methylols which can form methylene bridges with amines and therefore be integral to cellular stabilization. It was noted in several experiments that the use of hexamethylenetetramine alone was not effective in cellular stabilization, while the ammonium citrate/formaldehyde/ inhibitors combination of the present invention was effective.

The totality of the NMR data demonstrated that various chemically reactive species are rapidly generated from the combination of ammonium citrate and formaldehyde in further combination with the inhibitors. The reactive species or complexes varied with the nature and concentration of the reagent composition and slowly changed over time. The combination of the inhibitors and optional components used in the reagent composition of this invention, as well as the use of other ammonium salts likely produce additional reactive chemical species. The selection of reagent combinations and formulations for cellular stabilization was conducted based on selecting optimized reagent formulation to meet the cellular stabilization specifications. Thus the reagent formulations with appropriate functional performance can easily be used to produce, identify, isolate and manufacture specific chemically reactive species, from said combination, and used separately for cellular stabilization.

Example 2

The Reagent Composition Formulae

Additional experiments were designed and displayed utilizing the Design-Expert Version 5.0.8 statistical software produced by Stat-Ease Corporation, Minneapolis Minn. 55413. Such experiments were used to test ranges of concentrations and components for optimization of the stabilization reagent composition using response surface statistical methods for process optimization and modeling contained within the software algorithms. The ranges of the components of the stabilization reagent composition of this invention that were tested are indicated in Table 2.

TABLE 2

Components and Ranges of Stabilization Reagent

| Solution Component | Examples of Component | Range of concentrations |
|---|---|---|
| Ammonium salt(s) | ammonium citrate (dibasic), ammonium citrate (tribasic) | Up to 0.14 M |
| Formaldehyde | Paraformaldehyde (aq) or formaldehyde gas dissolved into liquid, or formalin | Up to about 0.8% by volume in water |
| Alkaline phosphatase inhibitor(s) | Tetramisole Pyrophosphate (10*H2O) | 10–60 mM Up to 50 mM |
| Protease inhibitor(s) | PMSF AEBSF | Up to 10 mM Up to 10 mM |
| Optional buffer | ADA (3.2%) or Pyrophosphate (123 mM) | Up to 50% by volume |

In the formulation of various Stabilization Reagent Compositions of this invention, the reactants that form liquid formaldehyde or paraformaldehyde by hydrolysis may differ. As indicated below, the ammonium ion source may also differ. Similarly the selection of alkaline phosphatase and protease inhibitors and/or combinations thereof may differ. It is anticipated that multiple alkaline phosphatase inhibitors are desirable in the reagent composition, in order to reduce the toxicity thereof, while obtaining the desired inhibition.

In the following experiments and in Examples 3–7, Solution A is a combination of ammonium citrate, the phosphatase inhibitors, and a protease inhibitor, specifically containing 57.06 mg/ml ammonium citrate, dibasic with the alkaline phosphatase inhibitors (9.63 mg/mL tetramisole- .HCl and 44.64 mg/mL sodium pyrophosphate, decahydrate), and the serine protease inhibitor (0.096 mg/mL AEBSF).

Solution B is a 0.05% formaldehyde solution in phosphate buffered saline.

Solution C comprises 10 mg/mL paraformaldehyde, 0.4 mL/mL sodium hydroxide, 1N and 60.5 mg/mL Tris buffer.

Control or PBS is a phosphate buffered saline solution.

Solution A+B or A/B or "Stabilization Reagent" as used below is the result of mixing 1 part by volume of Solution A with 1 part by volume Solution B.

Solution A+C or A/C as used below is the result of mixing 1 part by volume of Solution A with 1 part by volume of Solution C, to produce another Stabilization Reagent of the invention.

To determine the effect of differing buffers, pH and osmolarity on the Stabilization Reagent of this invention, a fresh normal blood sample was drawn into EDTA anticoagulant then mixed 1:1 with either Solution A alone, Solution B alone, Control, Solution A+B or Solution A+C within 1 hour of drawing. The pH and osmolarity measurements were made immediately after mixing with the blood samples or more than 1 hour after the mixing.

After 72-hour storage at 22° C., the samples were stressed by the addition of a the platelet activating agent, i.e., Phorbol 12-myristate 13-acetate (PMA) at a final concentration of 11.58 μM (see Example 3). The sample was stained with monoclonal antibodies to the platelet antigens CD41 (anti-CD41 FITC) and antibodies to platelet granule marker CD62p (anti-CD62p). An immune platelet count (IMPC) was performed according to the method of the International Council for Standardization in Haematology, cited above. The results are illustrated in Table 3 below.

TABLE 3

Effect of Buffer Changes in Stabilization Reagent

| Solutions: | Sol'n A | Sol'n B | Sol'n C | PBS | A/B | A/C |
|---|---|---|---|---|---|---|
| Average % Change in IMPC over 72 hours: activated | −41.33 | 22.32 | 5.50 | −214.48 | −1.98 | −8.03 |
| Average Change in % CD62+ in 72 hours: activated | −1.70 | −84.14 | −89.65 | −2.59 | −0.48 | −0.86 |

The combination of Solutions A and B or Solution A and C are superior in maintaining the IMPC and the expression of CD62p over the 72 hours of storage, than any of the solutions alone or the control PBS. This experiment demonstrates that the use of organic or inorganic buffers to adjust the pH of the combined or separate reagents does not limit the scope or practice of this invention.

Table 4 demonstrates the variation in the pH and osmolarity measurements of the blood samples containing the different solutions measured immediately after mixing with the blood sample (0 time) or more than one hour after mixing.

TABLE 4

Comparison of pH and Osmolarity Measurements

| | Immediately upon mixing (0 time) | | >1 Hour after mixing | |
|---|---|---|---|---|
| Solution | pH | Osmolarity | pH | Osmolarity |
| A | 5.77 | 747 | 5.77 | 757 |
| B | 7.35 | 462 | 7.34 | 467 |
| C | 7.18 | 433 | 7.20 | 434 |
| PBS/H$_2$O | 7.20 | 301 | 7.20 | 299 |
| A + B | 5.80 | 613 | 5.55 | 551 |
| A + C | 5.80 | 616 | 5.67 | 579 |

The optional buffer is included simply to bring the composition to physiological pH. The standard pH range tolerated for cell preservation is approximately between pH 7.8 and pH 5.0. The appropriate selection or need for buffer is thus readily within the skill of the art given these teachings.

Figure 9:
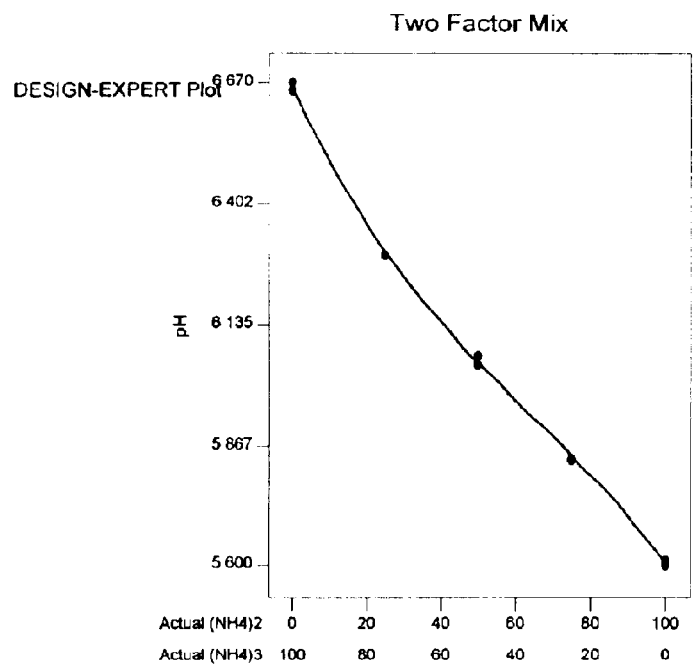
FIG. 9 is a graph showing pH ranges of the stabilization reagent of this invention at differing concentrations of ammonium ion in the ammonium salt solution. This graph demonstrates that the pH is associated with the type of $NH_4$ salt used and its concentration. Optional buffering is useful if the salt concentration that is used in the reagent does not produce the correct pH.

FIG. 9 is an example of the pH range produced within variations of the components listed. Thus, one of skill in the art, given the teachings contained herein, will expect that the addition of other basic or acidic, organic and inorganic compounds (as indicated by the use of Pyrophosphate or the organic buffer n-(2-Acetamido)-2-iminodiacetic acid (ADA)) would shift the range to higher or lower pH as desired.

Figure 10:
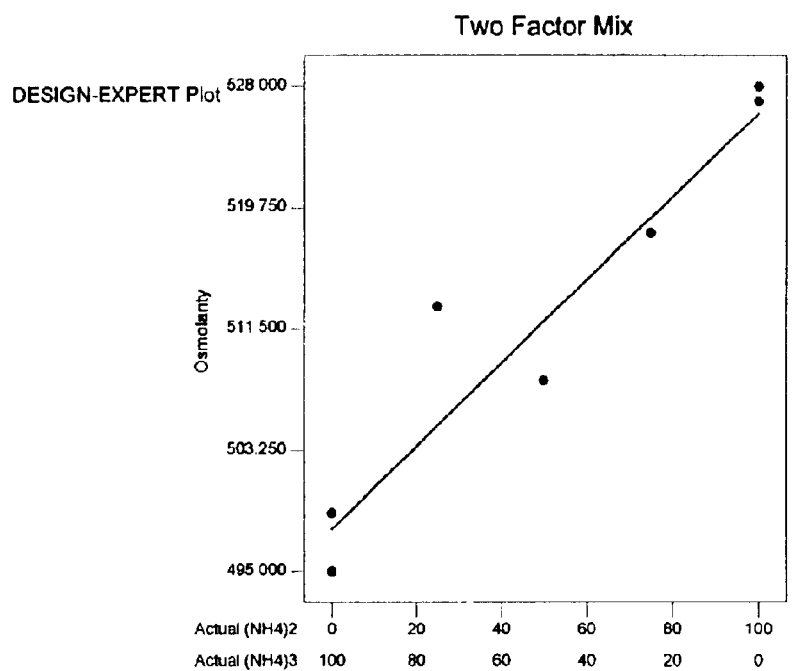
FIG. 10 is a graph showing the ranges of useful osmolarity for reagents containing differing concentrations of ammonium ion in the ammonium salt solution.

Similarly, the ranges of useful osmolarity for reagents of this invention may vary. The addition of components or the dilution with water can be easily accomplished to produce osmolarity ranges within the standard physiologic ranges of blood and urine, i.e., 250 to 1200 mOsmo. See, for example, FIG. 10.

Figure 11A:
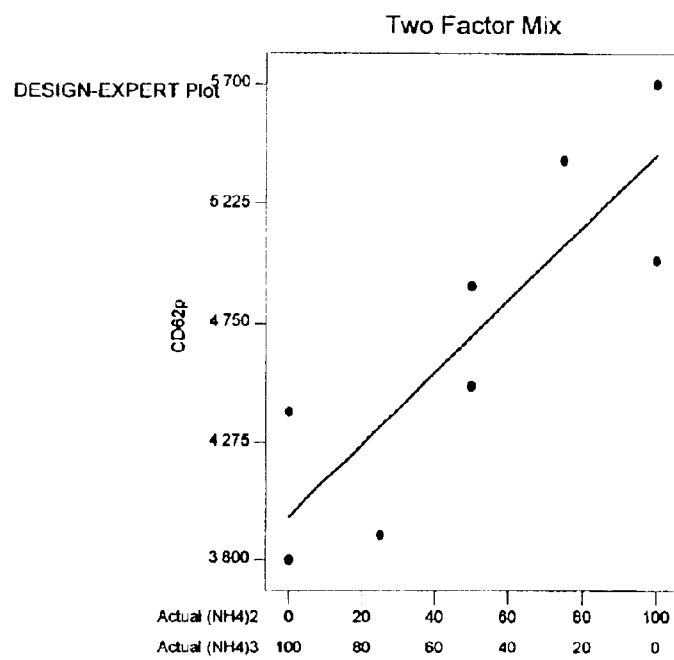
FIG. 11A is a graph showing that the use of dibasic ammonium citrate $(NH_4)_2$ provides better stabilization of CD62p than does tribasic ammonium citrate $(NH_4)_3$. Units are in CD62p percent.
Figure 11B:
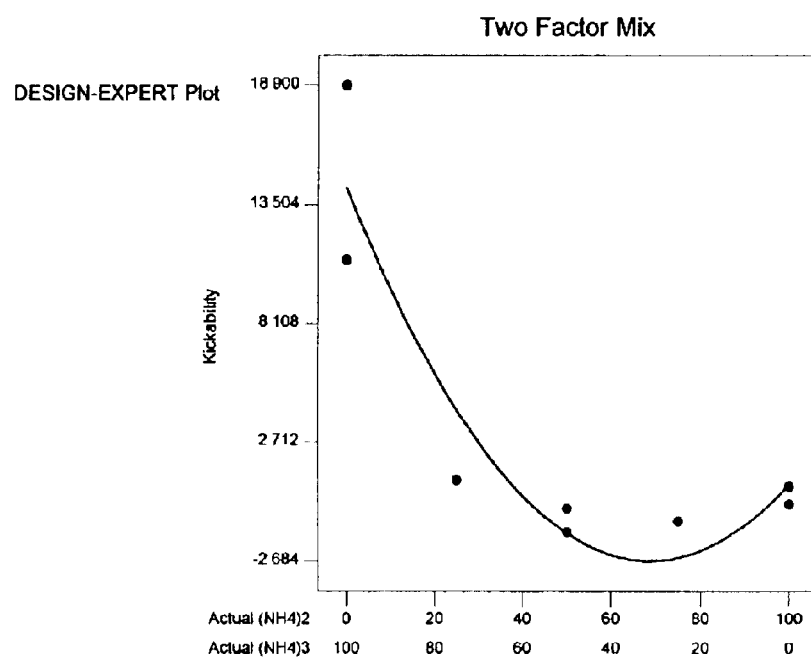
FIG. 11B is a graph showing the variation in Activation Potential at differing concentrations of ammonium ion in the ammonium salt solution. This graph indicates the degree of inhibition of response to external activation agents, in this case, PMA, associated with ammonium salt type and concentration, with all other factors held constant.

The maintenance of CD62p values when the reagent is added to blood is also variable within the above ranges of such components introduced into the stabilization reagent of this invention, e.g., component additions, pH and osmotic environment. These CD62p values are determinable via the optimization of selected reagents within statistically designed experiments. For example, FIGS. 11A and 11B demonstrate that this response is also determinable via the optimization of selected reagents within statistically designed experiments. FIGS. 11A and 11B show that the use of dibasic ammonium citrate [(NH$_4$)$_2$] provides better stabilization than does tribasic ammonium citrate [(NH$_4$)$_3$]. Statistical algorithms permitted the stabilization reagent of this invention to be tested on whole blood samples and contrasted with comparative testing using prior art (e.g., formaldehyde only) or commercial stabilization solutions.

Example 3

Comparison of Prior Art Components

The functional response of the platelets in their expression of CD62p is primary to one of the clinical applications of this invention and to the invention itself.

In one experiment, fresh normal blood was mixed 1:1 with Solution A, Solution B, a Control or the stabilization reagent (A+B) of this invention within 1 hour of drawing and the numbers of red blood cells (RBC) and percent difference in the numbers of platelets (PLT) measured on days 0 and 3.

The same protocol was conducted on activated blood samples. Activation means that the blood and associated platelets were stressed by the addition of a well documented, well defined, broad spectrum and ubiquitous platelet activating agent, i.e., Phorbol 12-myristate 13-acetate (PMA) at a final concentration of 11.58 μM. A PMA stock solution 100 μg/ml in dimethyl sulfoxide (DMSO) was used (0.162 mM Phorbol 12-myristate 13-acetate FW 616.8). Two μl PMA stock solution/ml blood (dilution 1/500) results in a final concentration of ~0.32 μM in blood. The activation process involves incubating 1 ml blood with 2 μl PMA for 10 minutes. Platelet activation potential (PAP) is the ability of the platelets to respond to the chosen activating agent as represented by a change in CD62p expression. PAP was assessed using 2 μl of a 1/100 dilution (0.0324 mM) of stock PMA is added with 10 μl antibodies and 100 μl of diluent (PBS) and 2.5 μl of blood and incubated for 15 minutes (final concentration of 11.58 μM).

It would be expected that cells that were appropriately stabilized would not respond to this activating agent, otherwise these same cells would be expected to change over time with storage and thus, at the time of analysis, not appropriately represent the natural in vivo state of the blood.

The following Tables 5A, 5B and 6 and FIGS. 1A through 8B demonstrate that the combination of reagents derived from various experimental designs produce results that are new and unique.

TABLE 5A

Fresh Blood Samples

| Donor (avg = 3) fresh blood samples treated with | RBC (Day 0) | PLT (Day 0) | RBC (Day 3) | PLT (Day 3) | Diff. RBC # | % Diff PLT |
|---|---|---|---|---|---|---|
| Solution A | 4.52 | 254.00 | 4.50 | 266.00 | −0.02 | 3.97 |
| Solution B | 4.23 | 256.67 | 4.49 | 304.67 | 0.26 | 17.56 |
| Control PBS | 4.42 | 242.00 | 4.52 | 243.33 | 0.10 | 1.66 |
| Solution A + B | 4.44 | 246.00 | 4.53 | 258.67 | 0.09 | 4.61 |

TABLE 5B

Activated Blood Samples

| Donor (avg = 3) activated blood samples treated with | RBC (Day 0) | PLT (Day 0) | RBC (Day 3) | PLT (Day 3) | Diff. RBC # | % Diff PLT |
|---|---|---|---|---|---|---|
| Solution A | 4.31 | 248.67 | 4.47 | 241.33 | 0.16 | −4.61 |
| Solution B | 4.25 | 250.00 | 4.45 | 282.00 | 0.21 | 12.51 |
| Control PBS | 4.66 | 252.67 | 4.61 | 127.33 | −0.05 | −52.49 |
| Solution A + B | 4.67 | 258.67 | 4.53 | 258.67 | −0.14 | −0.02 |

TABLE 6

Difference in CD62p+ platelets

% CD62+ platelets between Day 0 to Day 3

| Sample (Avg of 3 donors) | Treated with Solution A | Treated with Solution B | Treated with PBS | Treated with Solution A + B |
|---|---|---|---|---|
| Fresh blood samples | 78.28 | −3.99 | 38.06 | −0.22 |
| Activated blood samples | −1.70 | −84.14 | −2.59 | −0.48 |
| Platelet loss or gain: | 5% loss | 13% gain | 52% loss | 0.02% loss |

Although the individual reagents A and B, and even PBS maintained the red blood cell (RBC) and platelet (PLT) counts in normal blood, only the Stabilization Reagent(s) of this invention containing the above-listed combination of components maintained the platelet and RBC count and the expression of CD62p over 72 hours, as seen in Table 5A. A more dramatic difference is seen in Table 5B with the activated platelets. The individual components such as formaldehyde alone (Solution B) or ammonium citrate solution containing enzyme inhibitors pyrophosphate, tetramisole and AEBSF (Solution A) were not as effective as the combinations forming the Stabilization Reagents of the Invention. Thus the blood samples obtained from both normal donors and donors with activated platelets maintain their CD62p expression in the stabilization reagent of this invention in a state more representative of the in vivo state of their blood than in samples preserved with various preservatives or anticoagulants of the prior art.

Solution A demonstrates a 5% loss in platelets and a ~1.7% loss in CD62p expression. Solution B demonstrates an apparent gain of 13% of platelet number, probably associated with the loss of red blood cells in the sample (which are used to calculate the Immunoplatelet count), and a 84% loss in CD62p expression. PBS alone demonstrates a 52% loss of platelets; the percent expression of CD62p on the remaining platelets is therefore meaningless.

Example 4

Fresh EDTA-Treated Blood Preserved with the Reagent of this Invention Shows Normal CD62p Expression Fresh normal blood was drawn into EDTA anticoagulant then mixed 1:1 with the reagent of this invention (Stabilizer, Solutions A+B) of this invention within 1 hour of drawing. The sample was stained with monoclonal antibodies to the platelet antigens CD41 (anti-CD41 FITC) and antibodies to platelet granule marker CD62p (anti-CD62p). Using flow cytometry, with a gating for the sample set based in IgG1 isotype controls at 2%, the sample was analyzed.

Figure 1B:
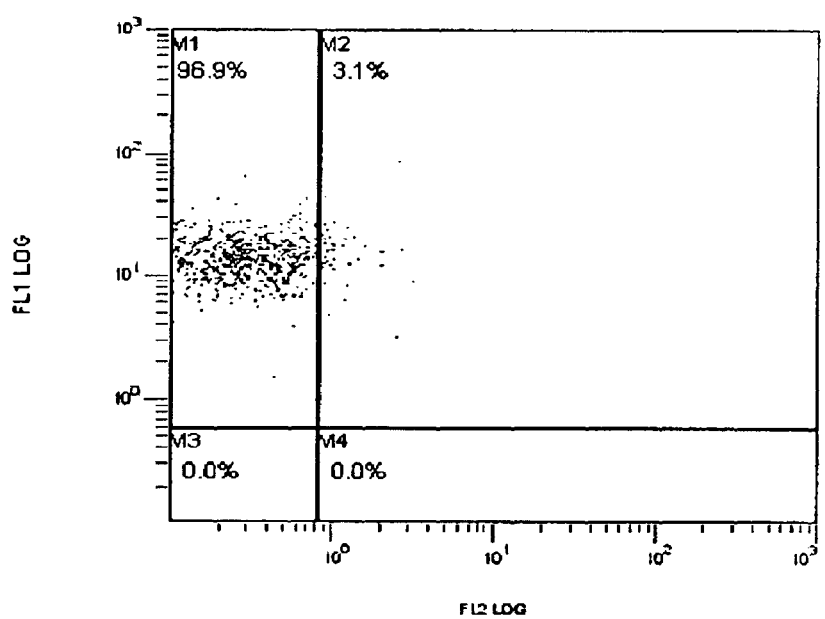
FIG. 1B is a histogram showing the CD41/CD62p (FL1log/Fl2log) expression of the components of the histogram of FIG. 1A.

The resulting histograms are shown in FIGS. 1A and 1B. Table 7 indicates the significant elements, including the mean fluorescence immunofluorescence (MFI) of the two antigen markers CD62p and CD41. The percentage positive CD62p platelets (platelets labeled with anti-CD62p antibody) is 3.1%.

TABLE 7

Fresh EDTA-Treated and Stabilized Samples

| Significant Elements | Events | % | MFI CD62p | MFI CD41 |
|---|---|---|---|---|
| Dual (coincidence) | 42 | 0.09 | 94.2 | 15 |
| Red Blood Cells | 50,000 | 93.95 | NA* | NA* |
| Platelets | 3,018 | 5.67 | 9.4 | 15.4 |
| Total Platelets | 3060 | 5.76 | 10.7 | 15.4 |
| Debris (not cells) | 39 | 0.08 | 7.3 | 0.3 |

*RBCs are negative for the CD62p expression

Example 5

Fresh Blood Activated with PMA and Maintained in the Reagent of the Invention Shows Platelet Expression of CD62p Fresh normal blood was drawn into EDTA anticoagulant and activated with Phorbol 12-myristate 13-acetate (PMA) using PMA stock 100 µg/ml in dimethyl sulfoxide (DMSO) (0.16 mM PMA, formula weight 616.8) at a concentration of 2 µl/ml blood (dilution 1/500), resulting in a final concentration of ~0.32 µM in the blood sample for 10 minutes. This activated sample is then mixed 1:1 in the stabilization reagent of this invention (STABILIZER) for 1 hour. This sample is stained with monoclonal antibodies to the platelet antigen CD41 (anti-CD41 FITC) and antibodies to platelet granule marker CD62p (anti-CD62p). Using flow cytometry, with a gating for the sample set based in IgG1 isotype controls at 2% positive set for the normal untreated sample, the sample was analyzed.

Figure 2A:
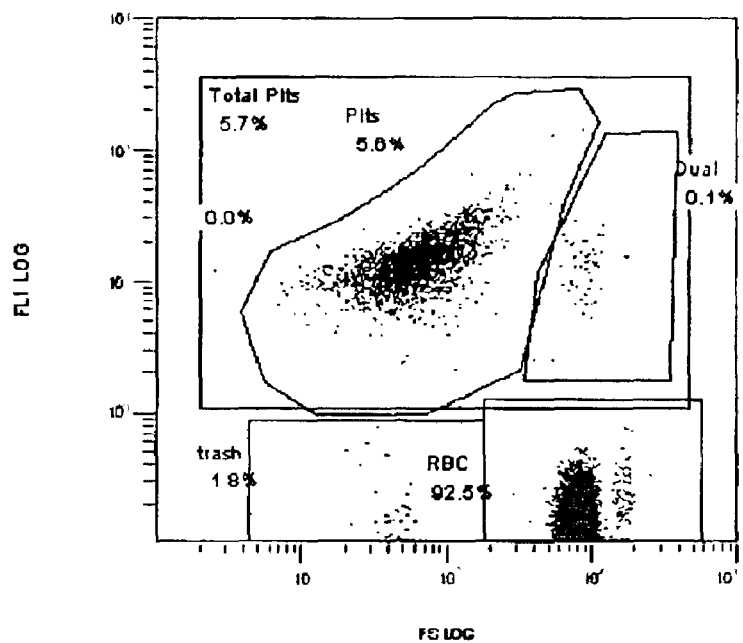
FIG. 2A is a histogram showing activated platelet expression of CD41 (FL1log/FSlog) maintained in the Stabilization Reagent of the present invention.
Figure 2B:
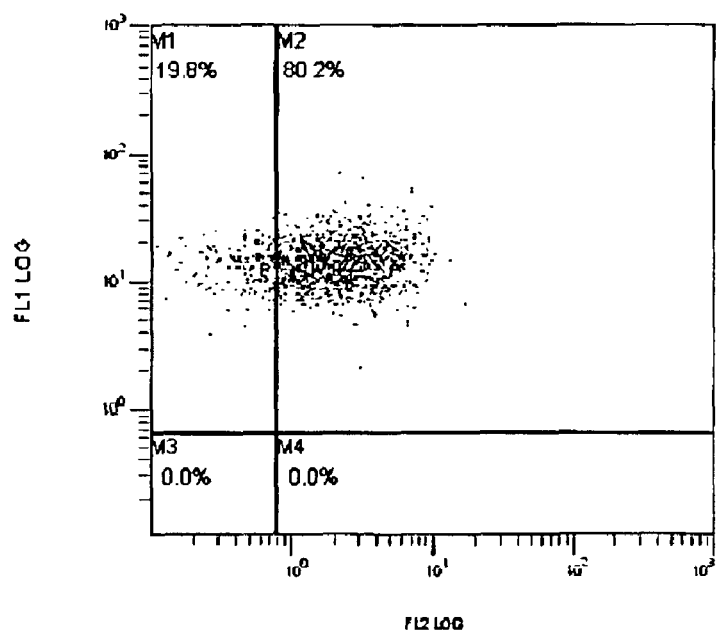
FIG. 2B is a histogram showing the CD41/CD62p (FL1log/Fl2log) expression of the components of the histogram of FIG. 2A.

The resulting histograms are shown in FIGS. 2A and 2B. Table 8 indicates the significant elements. The percentage positive CD62p positive (platelets labeled with anti-CD62p antibody) is 80.2%. Note that the percentage of platelets in the sample of blood (also containing RBCs and WBCs) is similar to the unactivated EDTA-treated sample.

TABLE 8

Pre-Activated, EDTA-treated and Stabilized Samples

| Significant Elements | Events | % | MFI CD62p | MFI CD41 |
|---|---|---|---|---|
| Dual (coincidence) | 54 | 0.11 | 90.3 | 13.3 |
| Red Blood Cells | 50,000 | 92.52 | NA* | NA* |
| Platelets | 2,955 | 5.6 | 7.1 | 15 |
| Total Platelets | 3,009 | 5.71 | 8.7 | 15 |
| Debris (not cells) | 885 | 1.77 | 4.5 | 0.1 |

*RBCs are negative for the CD62p expression

Example 6

Comparison of Fresh EDTA-Treated Blood Maintained in Commercial Stabilization Solutions or No Stabilization Solution For further comparison, two commercially available blood stabilization compositions are used in this examples in and in the following example, i.e., Commercial Reagent A is sold under the trademark StabilCyte Cell Stabilization Kit (BioE, St. Paul, Minn.). Commercial Reagent B is sold under the trademark Cyto-Chex Reagent (Streck Laboratories, La Vista, Nebr.).

A. Commercial Reagent A

Commercial Stabilizing Reagent A is added to a sample of blood withdrawn into EDTA according to manufacturer's instructions. After 1 hour, this sample is stained with monoclonal antibodies to the platelet antigen CD41 (anti-CD41 FITC) and antibodies to platelet granule marker CD62p (anti-CD62p). Using flow cytometry, with a gating for the sample set based on IgG1 isotype controls set at less than 0.2% of the sample or a gate set immediately above the CD62p and CD41 negative red blood cell population, the sample was analyzed.

Figure 3A:
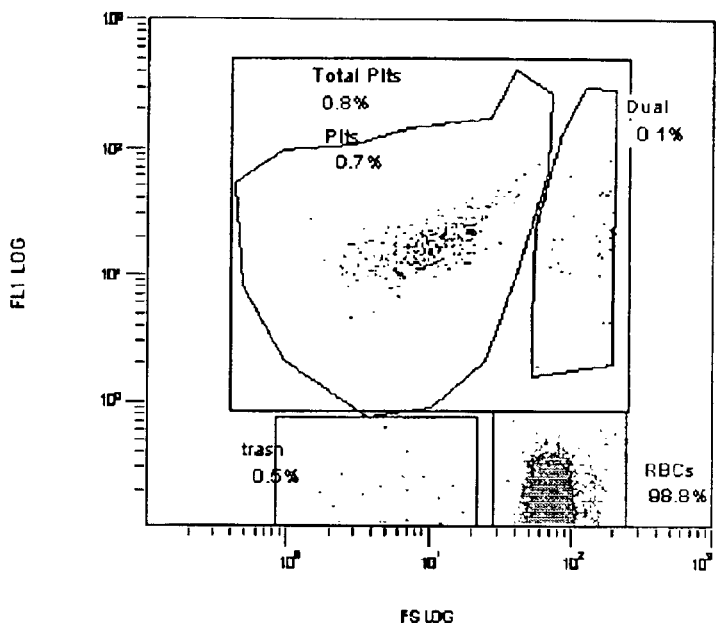
FIG. 3A is a histogram showing activated platelet expression of CD41 (FL1log/FSlog) maintained in a Commercial Stabilizing Reagent A.
Figure 3B:
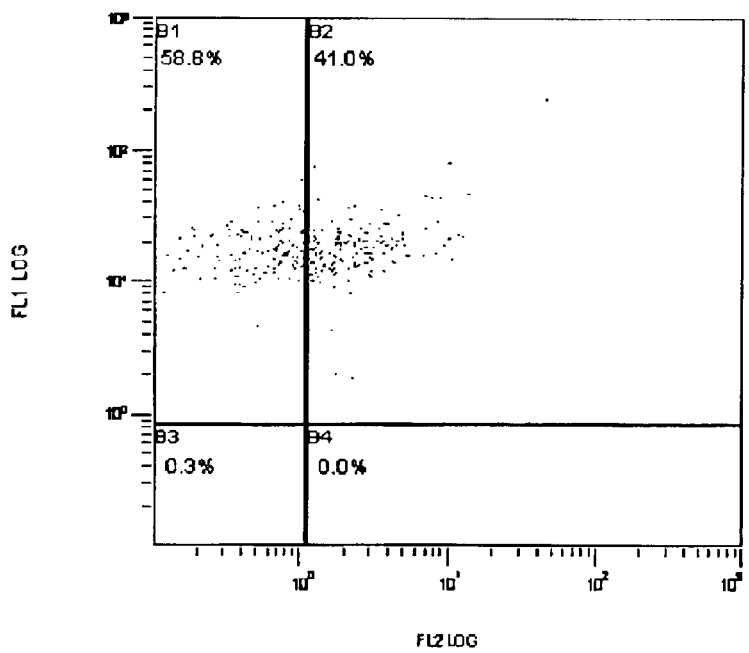
FIG. 3B is a histogram showing the CD41/CD62p (FL1log/Fl2log) expression of the components of the histogram of FIG. 3A.

The resulting histograms are shown in FIGS. 3A and 3B. Table 9 indicates the significant elements. There is an activation of the platelets producing a 41% positive CD62p population although no activation agent is added. There is also a loss of about 88% of the platelets in relation to the red blood cell (RBC) number.

TABLE 9

Fresh EDTA-treated Samples with Commercial Reagent A

| Significant Elements | Events | % | MFI CD62p | MFI CD41 |
|---|---|---|---|---|
| Dual (coincidence) | 33 | 0.07 | 139.3 | 30.7 |
| Red Blood Cells | 50,000 | 98.76 | NA* | NA* |
| Platelets | 345 | 0.68 | 12.1 | 19.5 |
| Total Platelets | 378 | 0.75 | 24.5 | 20.4 |
| Debris (not cells) | 238 | 0.48 | 5.3 | 0.1 |

*RBCs are negative for the CD62p expression

B. Commercial Reagent B

Commercial Stabilizing Reagent B is added to a sample of blood withdrawn into EDTA according to manufacturer's instructions. After 1 hour, this sample is stained with monoclonal antibodies to the platelet antigen CD41 (anti-CD41 FITC) and antibodies to platelet granule marker CD62p (anti-CD62p). Using flow cytometry, with a gating for the sample set based on IgG1 isotype controls set at less than 0.2% of the sample or a gate set immediately above the CD62p and CD41 negative red blood cell population, the sample was analyzed.

Figure 4A:
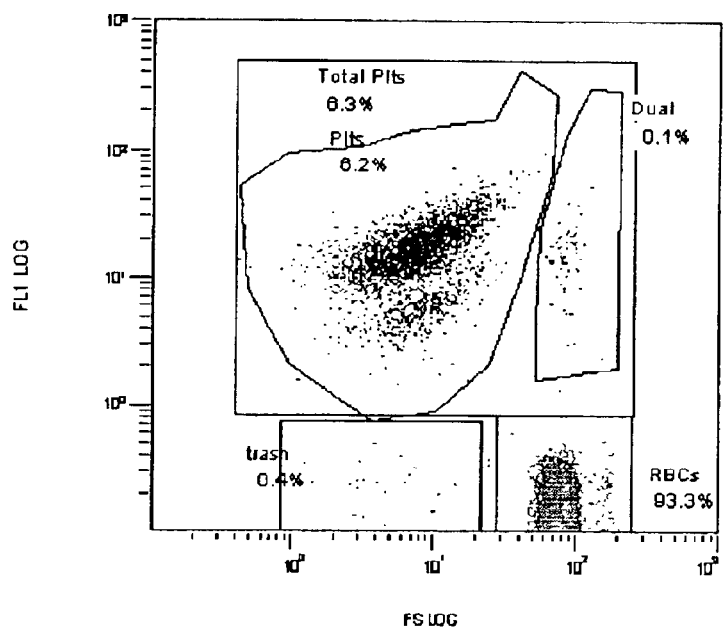
FIG. 4A is a histogram showing activated platelet expression of CD41 (FL1log/FSlog) maintained in a second Commercial Stabilizing Reagent B.
Figure 4B:
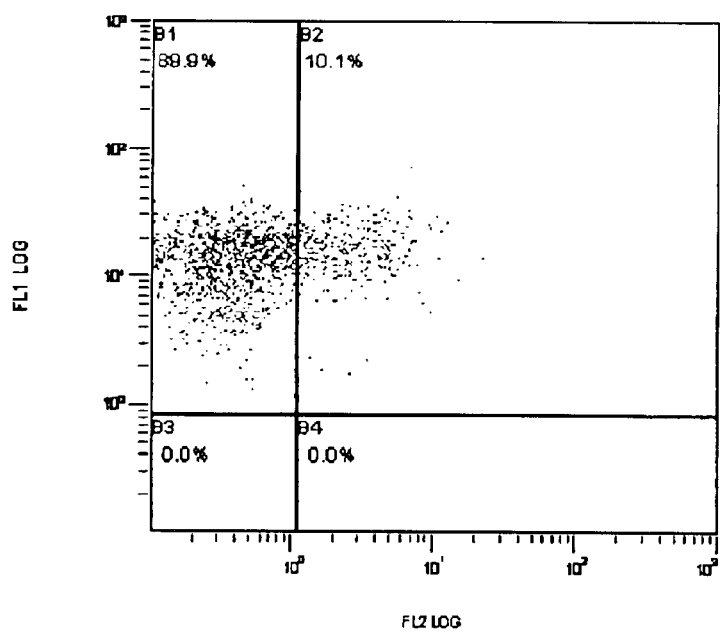
FIG. 4B is a histogram showing the CD41/CD62p (FL1log/Fl2log) expression of the components of the histogram of FIG. 4A.

The resulting histograms are shown in FIGS. 4A and 4B. Table 10 indicates the significant elements. The results illustrate an activation of the donor's platelets to 10.1% of the platelets being CD62p positive (see FIG. 4B). There is also a change in the light scatter, as seen by the split in the platelet population CD41/FS (forward light scatter), a portion of the platelets having decreased CD41 FITC (FL1 log) expression (see FIG. 4A).

TABLE 10

Fresh EDTA-treated Samples with Commercial Reagent B

| Significant Elements | Events | % | MFI CD62p | MFI CD41 |
|---|---|---|---|---|
| Dual (coincidence) | 61 | 0.12 | 87.8 | 17 |
| Red Blood Cells | 50,000 | 93.28 | NA* | NA* |
| Platelets | 3,322 | 6.2 | 9 | 17.5 |
| Total Platelets | 3,383 | 6.34 | 10.6 | 17.5 |
| Debris (not cells) | 180 | 0.36 | 5 | 0.1 |

*RBCs are negative for the CD62p expression

C. No Stabilization Reagent

A sample of blood was withdrawn into EDTA anticoagulant. After 1 hour, this sample is stained with monoclonal antibodies to the platelet antigen CD41 (anti-CD41 FITC) and antibodies to platelet granule marker CD62p (anti-CD62p). Using flow cytometry, with a gating for the sample set based on IgG1 isotype controls set at less than 0.2% of the sample or a gate set immediately above the CD62p and CD41 negative red blood cell population, the sample was analyzed.

Figure 5A:
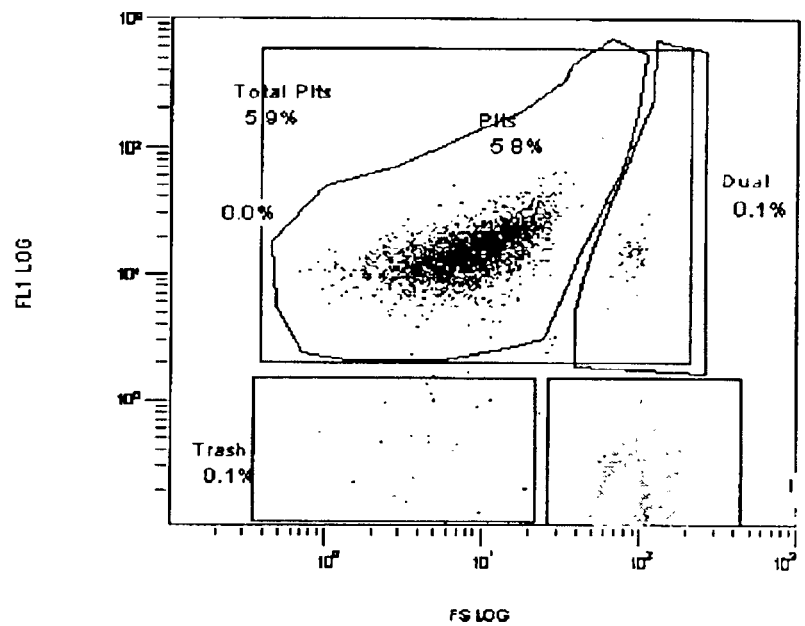
FIG. 5A is a histogram showing platelet expression of CD41 (FL1log/FSlog) maintained in normal blood treated with EDTA only.
Figure 5B:
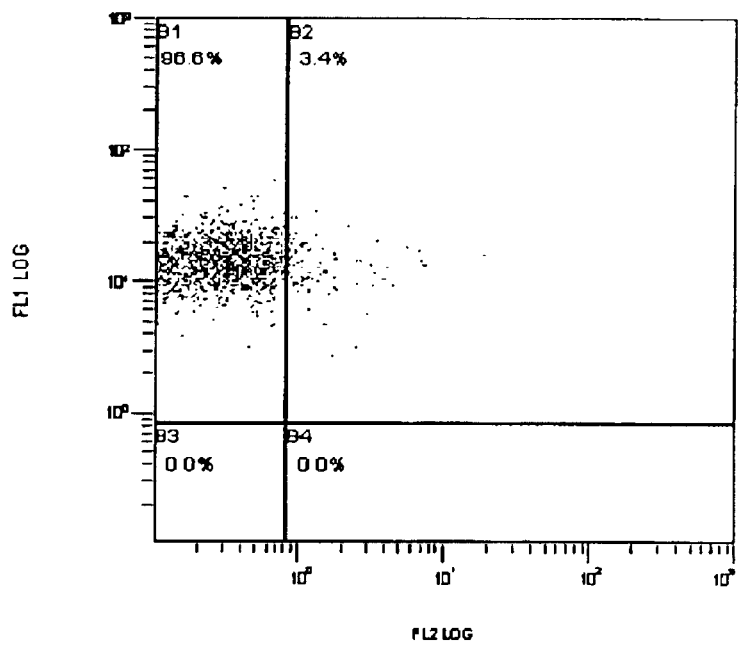
FIG. 5B is a histogram showing the CD41/CD62p (FL1log/Fl2log) expression of the components of the histogram of FIG. 5A.

The resulting histograms are shown in FIGS. 5A and 5B. Table 11 indicates the significant elements.

TABLE 11

Fresh EDTA-Treated Sample with No Reagent

| Significant Elements | Events | % | MFI CD62p | MFI CD41 |
|---|---|---|---|---|
| Dual (coincidence) | 45 | 0.09 | 90.5 | 14.8 |
| Red Blood Cells | 50,000 | 93.78 | NA* | NA* |
| Platelets | 3,100 | 5.81 | 9.7 | 16.6 |
| Total Platelets | 3,145 | 5.91 | 10.9 | 16.6 |
| Debris (not cells) | 27 | 0.06 | 5.4 | 0.5 |

*RBCs are negative for the CD62p expression

Example 7

Fresh EDTA-Treated Blood Preserved with a Stabilization Reagent and Stored for 7 Days A. The Reagent of this Invention Fresh normal blood was drawn into EDTA anticoagulant then mixed 1:1 with the reagent (Stabilizer) of this invention within 1 hour of drawing. The sample was kept at room temperature for seven days and then stained with monoclonal antibodies to the platelet antigens CD41 (anti-CD41 FITC) and antibodies to platelet granule marker CD62p (anti-CD62p). Using flow cytometry, with a gating for the sample set based on IgG1 isotype controls set at less than 0.2% of the sample or a gate set immediately above the CD62p and CD41 negative red blood cell population, the sample was analyzed.

Figure 6A:
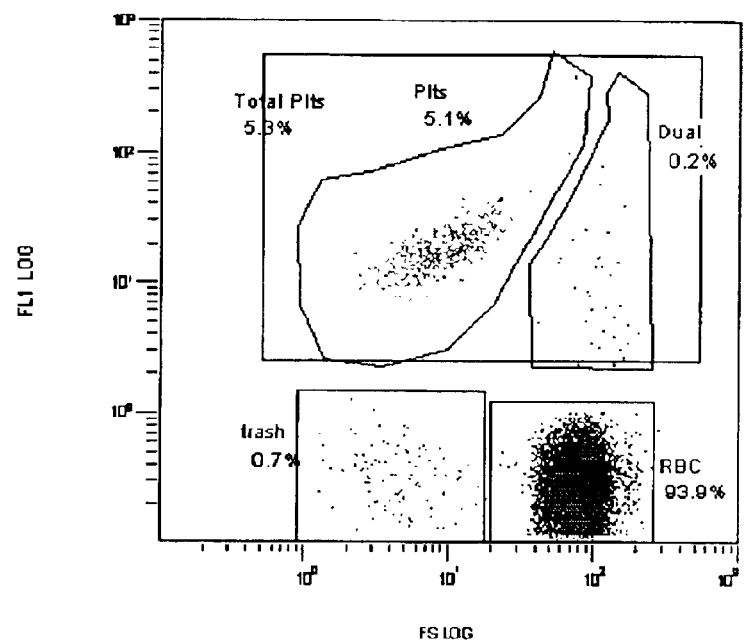
FIG. 6A is a histogram showing activated platelet expression of CD41 (FL1log/FSlog) maintained in normal blood treated with the Stabilization Reagent of the invention and stored at 22° C. for 7 days.
Figure 6B:
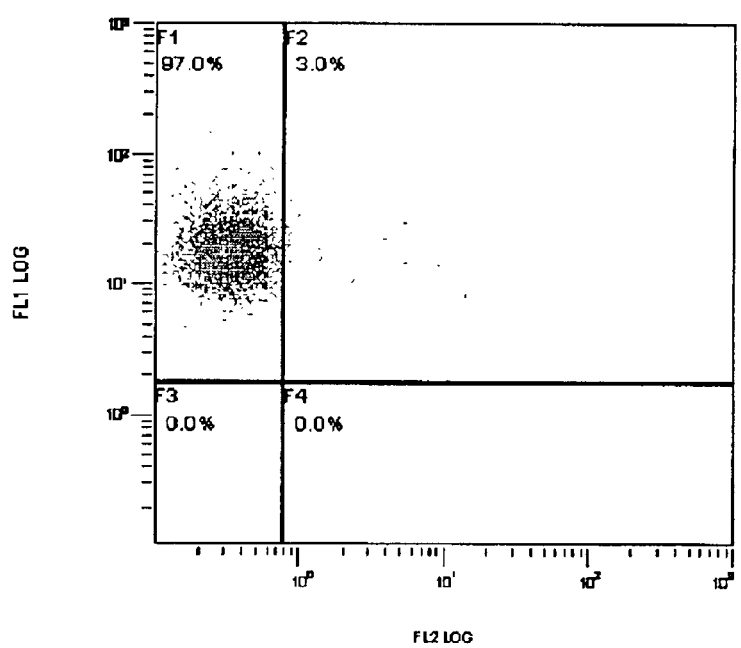
FIG. 6B is a histogram showing the CD41 expression of the components of the histogram of FIG. 6A.

The resulting histograms are shown in FIGS. 6A and 6B. Table 12 indicates the significant elements, including the mean fluorescence imunofluorescence (MFI) of the two antigen markers CD62p and CD41. The sample maintains its integrity within less than 5% of the level of CD62p activation seen within one hour of stabilization (see Example 4, FIGS. 1A and 1B and Table 7). The platelet percentage of total cell (5.3%) is also maintained within 5%.

TABLE 12

Fresh EDTA-treated and Stabilized Samples Stored 7 Days

| Significant Elements | Events | % | MFI CD62p | MFI CD41 |
| --- | --- | --- | --- | --- |
| Dual (coincidence) | 124 | 0.23 | 114.7 | 13.2 |
| Red Blood Cells | 50,000 | 93.9 | NA* | NA* |
| Platelets | 2,705 | 5.08 | 11.2 | 20.8 |
| Total Platelets | 2,825 | 5.3 | 15.5 | 20.5 |
| Debris (not cells) | 393 | 0.74 | 5.5 | 0.4 |

*RBCs are negative for the CD62p expression

B. Commercial Stabilization Reagent B

Fresh normal blood was drawn into EDTA anticoagulant then mixed 1:1 with the Solution B within 1 hour of drawing. The sample was kept at room temperature for seven days and then stained with monoclonal antibodies to the platelet antigens CD41 (anti-CD41 FITC) and antibodies to platelet granule marker CD62p (anti-CD62p). Using flow cytometry, with a gating for the sample set based on IgG1 isotype controls set at less than 0.2% of the sample or a gate set immediately above the CD62p and CD41 negative red blood cell population, the sample was analyzed.

Figure 7A:
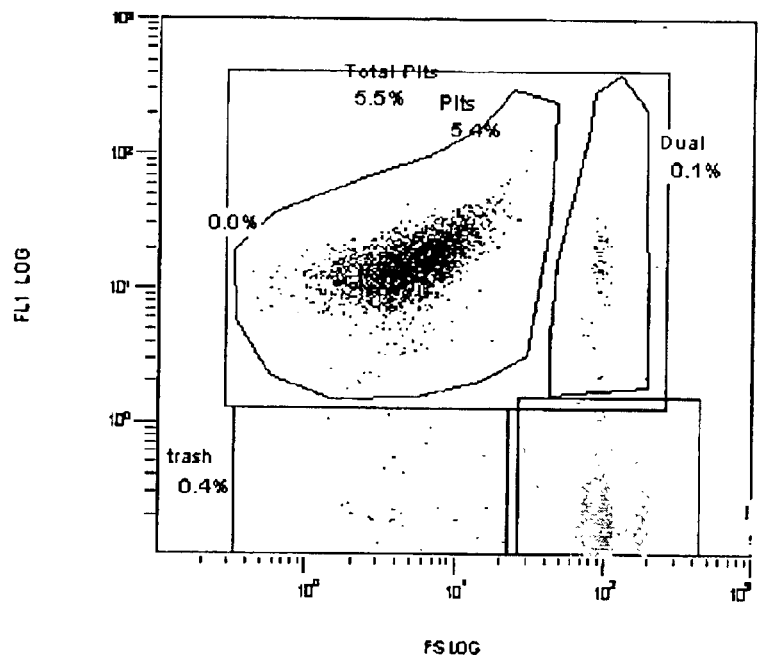
FIG. 7A is a histogram showing activated platelet expression of CD62p maintained in normal blood treated with EDTA and Commercial Stabilizing Reagent B and stored at 22° C. for 7 days.
Figure 7B:
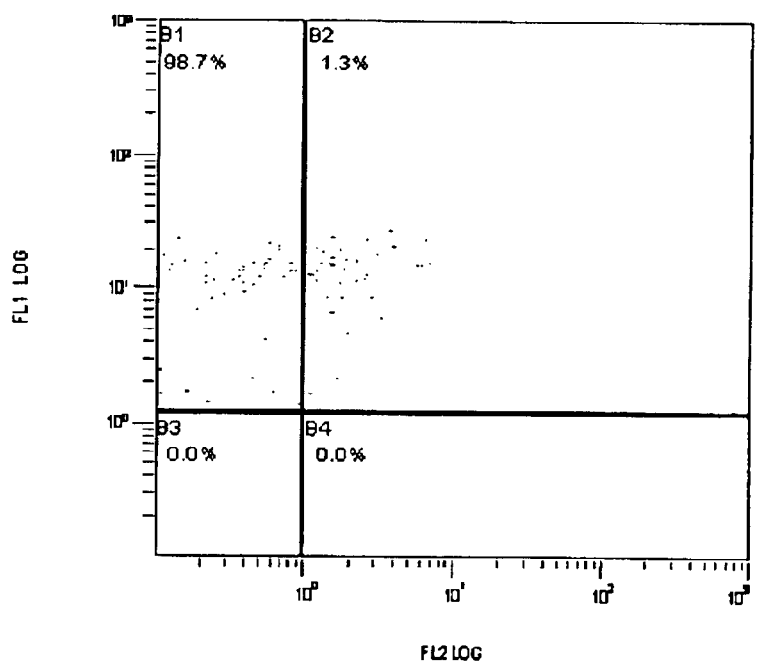
FIG. 7B is a histogram showing the CD41 expression of the components of the histogram of FIG. 7A.

The resulting histograms are shown in FIGS. 7A and 7B. Table 13 indicates the significant elements, including the mean fluorescence imunofluorescence (MFI) of the two antigen markers CD62p and CD41. Although Solution B appears to maintain platelet number and a low CD62p activation (1.3%), this value has changed significantly from the one hour value of 10.1% (see Example 5, FIGS. 4A and 4B and Table 8). Thus, the CD62p % positive value was not maintained in the stored sample and this sample would not be suitable for accurate diagnostic interpretation.

TABLE 13

Fresh EDTA-treated and Commercial Reagent B-Stabilized Samples Stored 7 Days

| Significant Elements | Events | % | MFI CD62p | MFI CD41 |
| --- | --- | --- | --- | --- |
| Dual (coincidence) | 47 | 0.09 | 94.5 | 15.5 |
| Red Blood Cells | 50,000 | 94.12 | NA* | NA* |
| Platelets | 2,875 | 5.41 | 5.6 | 16.7 |
| Total Platelets | 2,928 | 5.51 | 7.3 | 16.7 |
| Debris (not cells) | 189 | 0.36 | 5.8 | 0.1 |

*RBCs are negative for the CD62p expression

C. Commercial Stabilization Reagent A

Fresh normal blood was drawn into EDTA anticoagulant then mixed 1:1 with the Solution A within 1 hour of drawing. The sample was kept at room temperature for seven days and then stained with monoclonal antibodies to the platelet antigens CD41 (anti-CD41 FITC) and antibodies to platelet granule marker CD62p (anti-CD62p). Using flow cytometry, with a gating for the sample set based on IgG1 isotype controls set at less than 0.2% of the sample or a gate set immediately above the CD62p and CD41 negative red blood cell population, the sample was analyzed.

Figure 8A:
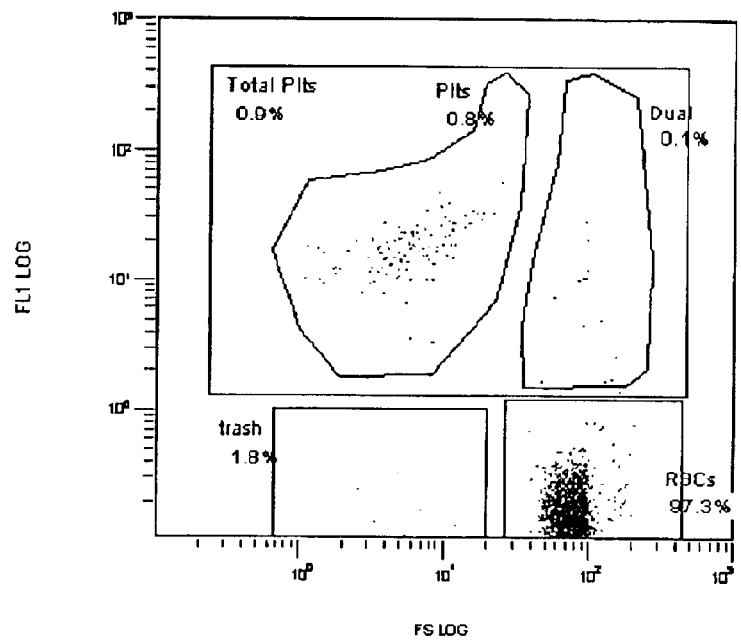
FIG. 8A is a histogram showing activated platelet expression of CD62p maintained in blood treated with EDTA and Commercial Stabilizing Reagent A and stored at 22° C. for 7 days.
Figure 8B:
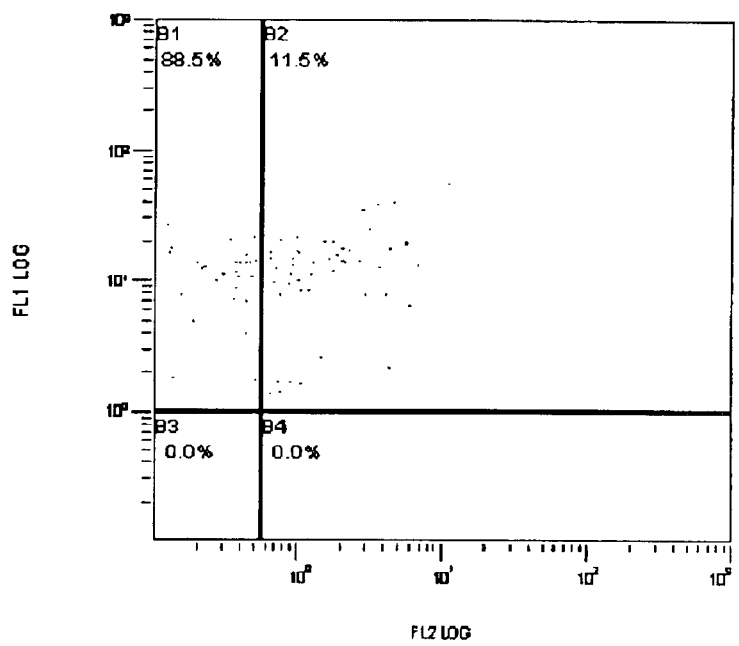
FIG. 8B is a histogram showing the CD41 expression of the components of the histogram of FIG. 8A.

The resulting histograms are shown in FIGS. 8A and 8B. Table 14 indicates the significant elements, including the mean fluorescence imunofluorescence (MFI) of the two antigen markers CD62p and CD41. The blood sample preserved in Solution A does not maintain platelet number or CD62p activation (11.5%); this value has changed significantly from the one hour value of 41% (see Example 6, FIGS. 3A and 3B and Table 9). Thus, this sample would not be suitable for accurate diagnostic interpretation.

TABLE 14

| Significant Elements | Events | % | MFI CD62p | MFI CD41 |
| --- | --- | --- | --- | --- |
| Dual (coincidence) | 34 | 0.07 | 100.3 | 11.6 |
| Red Blood Cells | 50,000 | 98.53 | NA* | NA* |
| Platelets | 410 | 0.81 | 6.8 | 19.9 |
| Total Platelets | 447 | 0.88 | 14.5 | 19.2 |
| Debris (not cells) | 296 | 0.58 | 5.2 | 0.1 |

*RBCs are negative for the CD62p expression

All documents cited above are incorporated by reference herein.

What is claimed is:

1. A non-lytic blood cell sample stabilization reagent composition comprising:
   (a) reactants that generate multiple species of formaldehyde-ammonium complexes;
   (b) at least one inhibitor of phosphatase enzymatic activity; and
   (c) at least one inhibitor of protease enzymatic activity, wherein said composition stabilizes and preserves platelets present in samples containing blood cells.

2. The reagent composition according to claim 1, wherein said composition stabilizes the expression of CD62p on platelets in a blood sample for at least 24 hours after said blood sample is treated with said composition.

3. The reagent composition according to claim 2, wherein said blood sample further contains an anti-coagulant or a coagulation pathway inhibitor.

4. The reagent composition according to claim 3, wherein said anticoagulant or inhibitor is selected from the group consisting of ethylenediaminetetraacetic acid (EDTA), a citrate salt, heparin, sodium fluoride and hirudin, and mixtures thereof.

5. The reagent composition according to claim 2 wherein said stabilized expression of CD62p on platelets in said stabilized sample after 24 hours is ±20% of the number of CD62p positive platelets that would be found in said blood sample when measured immediately after withdrawal from the body in the absence of said composition.

6. The reagent composition according to claim 1, wherein said complexes are selected from the group consisting of: (a) a hexamethylenetetramine, (b) a methyleneimine, (c) a methylol; (d) a hemihexamine, (e) a cyclotrimethylenetriamine complex containing methylene bridged amino, amido and guanidyl groups; and (e) a complex that cross-links polypeptide chains or proteins with methylene bridges, wherein said polypeptide chains or proteins are present on the surfaces of said cells in said sample, and (f) combinations of (a) through (e).

7. The reagent composition according to claim 1, wherein said protease inhibitor is selected from the group consisting of: phenylmethansulfonyl fluoride (PMSF), 4-(2-aminoethyl)benzynesulfonyl fluoride hydrochloride (AEBSF), Aprotinin, diisopropyl phosphorofluoridate (DFP), α-toluenesulfonyl fluoride, entipain, chymostatin, leupeptin L-1-chloro-3-[4-tosyl-amido]-7-amino-2-heptanone-HCl (TLCK), L-1-chloro-3-[4-tosylamido]-4-phenyl-2-butanone (TPCK), E-64, amastatin, bestatin, diprotin, EDTA, pepstatin, and combination thereof.

8. The reagent composition according to claim 1, wherein said phosphatase inhibitor is selected from the group consisting of pyrophosphate, microcystin LA, microcystin LR, tetramisole, L-4-bromotetramisole, tautomycin, okadaic acid, calyculin, thrysiferyl-23-acetate, cantharidine, vanadium salts, sodium orthovanadate, tartrate salts, phloridzin, molybdate salts, imidazole, and combinations thereof. formaldehyde and an ammonium salt solution.

9. The reagent composition according to claim 1, further comprising an organic basic compound for adjusting the pH range to be within pH 4.5 to 8.0.

10. The reagent composition according to claim 1, characterized by a molarity of between 0.01 and 1 molar.

11. The composition according to claim 1, wherein said reactants comprise a non-lytic ammonium salt solution.

12. The composition according to claim 11, wherein said reactants comprise an aliphatic aldehye of between 1 to 4 carbon atoms and a non-lytic ammonium salt solution.

13. The composition according to claim 12, wherein said reactants comprise formaldehye and a non-lytic ammonium salt solution.

14. The reagent composition according to claim 11, wherein said non-lytic ammonium salt is selected from the group consisting of ammonium citrate, ammonium sulfate, ammonium persulfate, ammonium sulfamate, ammonium acetate, ammonium carbamate, ammonium carbonate, ammonium phosphate, ammonium lactate, ammonium tartrate, ammonium thiocyanate, ammonium hydroxide, and a combination of any of said ammonium salts.

15. The composition according to claim 11, wherein said reactants comprise paraformaldehyde and a non-lytic ammonium salt solution.

16. A non-lytic blood cell sample stabilization reagent composition comprising:
    (a) paraformaldehyde and a non-lytic ammonium salt solution;
    (b) at least one inhibitor of phosphatase enzymatic activity; and
    (c) at least one inhibitor or protease enzymatic activity,
wherein said paraformaldehyde and ammonium salt solution generates multiple species of formaldehyde-ammonium complexes and wherein said composition stabilizes and preserves platelets present in samples containing blood cells.

17. A non-lytic blood cell sample stabilization reagent composition comprising:
    (a) a compound that upon hydrolysis generates formaldehyde and a non-lytic ammonium salt;
    (b) at least one inhibitor of phosphatase enzymatic activity; and
    (c) at least one inhibitor of protease enzymatic activity,
    wherein said compound and said ammonium salt generate multiple species of formaldehyde-ammonium complexes and wherein said composition stabilizes and preserves platelets present in samples containing blood cells.

18. The composition according to claim 17, wherein said compound is selected from the group consisting of ethylene oside and propylene oxide.

19. A non-lytic blood cell sample stabilization reagent composition comprising:
    (a) reactants that generate multiple species of formaldehyde-ammonium complexes;
    (b) at least one inhibitor of phosphatase enzymatic activity;
    (c) at least one inhibitor of protease enzymatic activity; and
    (d) an inorganic basic salt or an organic basic compound for adjusting the pH range of said composition to within pH 4.5 to 8.0,
wherein said composition stabilizes and preserves platelets present in samples containing blood cells.

20. A non-lytic blood cell sample stabilization reagent compositioin comprising:
    (a) reactants that generate multiple species of formaldehyde-ammonium complexes;
    (b) at least one inhibitor of phosphatase enzymatic activity;
    (c) at least one inhibitor of protease enzymatic activity, and
    (d) a buffer that provides a physiological pH,
wherein said composition stabilizes and preserves platelets present in samples containing blood cells.

21. The reagent according to claim 20, wherein said buffer is selected from the group consisting of phosphate buffered saline, isotonic saline, Tris buffer, N-(2-Acetamido)-2-iminodiacetic acid Pyrophosphate buffer acetate buffer, acetate buffer, succinate buffer, maleate buffer, citrate buffer, imidazole buffer, carbonate buffer, MES buffer, MOPS buffer, HEPES buffer, and combinations thereof.

22. A kit comprising at least two separate components for admixture into a non-lytic platelet stabilization reagent, said components comprising:
    (a) a first component, which is an aliphatic aldehyde of between 1 to 4 carbon atoms or paraformaldehyde in liquid or powder form or reactants that upon hydrolysis generate formaldehyde or paraformaldehyde, in an optional buffer,
    (b) a second component, which is a solution comprising a non-lytic ammonium salt solution, wherein said second component has a physiological pH;
    (c) a third component, which is at least one inhibitor of phosphatase enzymatic activity and is optionally provided in admixture with said second component; and
    (d) a fourth component, which is at least one inhibitor of protease enzymatic activity and is optionally provided in admixture with said second component.

23. The kit according to claim 22, wherein said inhibitor (c) is provided as a part of the ammonium salt solution of (b).

24. The kit according to claim 22, wherein said inhibitor (d) is provided as part of the ammonium salt solution of (b).

25. The kit according to claim 22, wherein said first component (a) is provided as a separate component distinct from components (b), (c) and (d).

26. The kit according to claim 22, wherein said inhibitors (c) and (d) are provided as part of the ammonium salt solution of component (b).

27. The kit according to claim 22, wherein said component (c) and (d) are provided in combination in a separate component distinct from components (a) and (b).

28. The kit according to claim 22, wherein said component (a) is a 1% aqueous formaldehyde solution.

29. The kit according to claim 22, wherein said component (b) contains a buffer.

30. The kit according to claim 22, further comprising platelet monoclonal antibody-dye conjugates.

31. The kit according to claim 22, further comprising instructions and reagents for performing measurement CDβp antigen expression on platelets.

32. The method according to claim 22, further comprising at least one of the following additional components selected from the group consisting of suitable vessels for containing samples, suitable controls or tables of normal or disease-characteristic values of activated platelets; an anti-coagulant or coagulation pathway inhibitor, a monoclonal antibody and a marker suitable for the performance of flow cytometric analyses and combinations thereof; suitable diluents and buffers for the samples, disposable gloves, decontamination instruction, applicator sticks or containers, and sample preparator cups.

33. A method for assessing the efficacy of a non-lytic blood cell stabilizing reagent comprising the steps of:
  (a) measuring activation of platelets expressing CD62p by contacting a blood sample which has been treated with the composition of claim 1 and an activating material that activates cellular response by causing physical and/or enzymatic changes in platelets
  (b) optionally storing said sample at 20 to 25° C. for up to 72 hours; and
  (c) determining the change in expression of CD62p on platelets in said sample compared with the expression of CD62p on platelets in a sample that has not been treated with said reagent composition,
  wherein stabilization is demonstrated when the percentage of platelets expressing CD62p in said reagent treated samples is less than that percentage in an untreated sample stored for the same duration.

34. The method according to claim 33, wherein said activating material is a solution of phorbol 12-myristate and 13-acetate (PMA).

35. The method according to claim 34, wherein said PMA is added to a final concentrationof 0.001–5 μM in said sample.

36. The method according to claim 35, wherein said blood sample is treated with an anti-coagulant or coagulation pathway inhibitor.

37. The method according to claim 35, wherein said change in percentage of CD62p platelets indicative of stabilization is measured by flow cytometry according to the formula:

(Parameter C minus Parameter A) >(Parameter D minus Parameter B), wherein Parameter A is the percentage of CD62p positive platelets in an anticoagulated blood sample containing no stabilization reagent composition;
wherein Parameter B is the percentage of CD62p positive platelets in an anticoagulated blood sample incubated with the stabilization reagent composition for one hour;
wherein Parameter C is the percentage of CD62p positive platelets in an anticoagulated blood sample containing no stabilization reagent composition to which said PMA is added to concentration between 0.001 μM and incubated for up to one hour; and
wherein Parameter D is the perentage of CD62p positive platelets in the anticoagulated blood sample containing the stabilization reagent to which PMA is added to a concentration between 0.001 μM and 5 μM and incubated for up to one hour.

38. The method according to claim 37, wherein the difference in the percentage of CD62p positive platelets as represented by the formula Parameter D minus Parameter B is less than 20% of that value determined within the first hour after addition of said PMA.

39. A non-lytic blood cell sample stabilization reagent composition comprising:
  (a) reactants that generate multiple species of formaldehyde-ammonium complexes;
  (b) an effective amount of at least one inhibitor of phosphatase enzymatic activity at a concentration up to 120 mM; and
  (c) an effective amount of at least one inhibitor of protease enzymatic activity at a concentration up to 10 mM,
  wherein said compositions stabilizes and preserves platelets present in samples containing blood cells.

40. A stabilized blood cell composition comprising:
  (i) a blood cell sample comprising platelets; and
  (ii) a non-lytic reagent composition comprising:
    (a) reactants that generate multiple species of formaldehye-ammonium complexes;
    (b) at least one inhibitor of phosphatase enzymatic activity; and
    (c) at least one inhibitor of protease enzymatic activity,
    wherein said composition comprises stabilized and preserved platelets.

41. The stabilized composition according to claim 40, wherein said composition retains a stabilized expression of CD62p on platelets in said sample for at least 24 hours after said sample is treated with said composition, and wherein said treated sample maintains ±20% of the number of CD62p positive platelets that would be found in said sample, when said sample is measured immediately after withdrawal from the body.

42. A method of stabilizing blood cells in a sample containing platelets, said method comprising:
  treating said sample with a non-lytic reagent composition comprising:
    (a) reactants that generate multiple species of formaldehyde-ammonium complexes;
    (b) at least one inhibitor of phosphatase enzymatic activity; and
    (c) at least one inhibitor of protease enzymatic activity; and
  incubating the resulting sample-reagent composition mixture at room temperature for at least one hour.

43. The method according to claim 42, wherein cells in said samples are characterized by a stabilized expression of CD62p on platelets in said sample for at least 24 hours after said treatment, and wherein said treated sample maintain ±20 % of the number of CD62p positive platelets that would be found in said sample, when said sampole is measured without treatment immediately after withdrawal from the body.

44. The method according to claim 43, further comprising the step of drawing sample into a calcium chelating anticoagulant or a coagulation pathway inhibitor prior to said treating step.

45. The method according to claim 43 or 44, further comprising the steps of:
  measuring platelet activation potential by containing said treated sample with an activating material that is known to activate cellular response by causing physical and/or enzymatic changes in platelets and an associated increase in CD62expression;
  optionally storing said samples at 20 to 25° C., for up to 72 hours; and determining the change in expression of CD62p on platelets in said treated sample compared with the expression of CD62p on platelets in a sample untreated with said reagent composition, wherein the percentage of platelets expressing the CD62p antigen in said reagent treated samples is less than that percentage in an untreated sample stored for the same duration.

46. The method according to claim 45, wherein said activating material is a solution of phorbol 12-myrisate 13-acetate (PMA).

47. The method according to claim 46, wherein said PMA is added to a final concentration of 0.001–5 $\mu$M in said sample.

48. The method according to claim 46, wherein said change in percentage of CD62p platelets indicative of stabilization is measured by flow cytometry according to formula:

(Parameter C minus Parameter A)>(Parameter D minus Parameter B), wherein Parameter A is the percentage of CD62p positive platelets in an anticoagulated blood sample containing no reagent composition;

wherein Parameter B is the percentage of CD62p positive platelets in an anticoagulated blood sample incubated with reagent composition for one hour;

wherein Parameter C is the percentage of CD62p positive platelets in an anticoagulated blood sample containing no reagent composition to which said PMA is added to a concentration between 0.001 $\mu$M and 5 $\mu$M amd incubated for up to one hour; and wherein Parameter D is the percentage of CD62p positive platelets in the anticoagulated blood sample containing the reagent composition to which PMA is added to a concentration betwen 0.001 $\mu$M and 5 $\mu$M and incubated for up to one hour.

49. The method according to claim 48, wherein the percentage of CD62p positive platelets in the treated sample does not change more than 20% within the first hour after addition of said PMA.

50. A kit comprising at least two separate components for admixture into a non-lytic platelet stabilization reagent, said components comprising:

(a) a first component, which is a paraformaldehyde and buffer solution, and (b) a second component, which is a solution comprising
   i. a non-lytic ammonium salt solution comprising ammonium citrate,
   ii. inhibitors of phosphatase enzymatic activity comprising tetramisole.HCl and sodium pyrophosphate decahydrate; and
   iii. an inhibitor of serine protease enzymatic activity comprising 4-(2-aminoethyl)benzene sulfonyl fluoride hydrochloride.

* * * * *